(12) United States Patent
Nelson

(10) Patent No.: US 9,872,893 B2
(45) Date of Patent: Jan. 23, 2018

(54) **ENDOLYSINS ACTIVE AGAINST *STAPHYLOCOCCUS* BACTERIA, PHARMACEUTICAL COMPOSITIONS, AND METHODS RELATING THERETO**

(71) Applicant: University of Maryland, College Park, College Park, MD (US)

(72) Inventor: Daniel C. Nelson, Rockville, MD (US)

(73) Assignee: University of Maryland College Park, College Park, MD (US)

( * ) Notice: Subject to any disclaimer, the term of this patent is extended or adjusted under 35 U.S.C. 154(b) by 0 days.

(21) Appl. No.: 14/794,186

(22) Filed: Jul. 8, 2015

(65) Prior Publication Data

US 2016/0038572 A1 Feb. 11, 2016

Related U.S. Application Data

(60) Provisional application No. 62/023,096, filed on Jul. 10, 2014.

(51) Int. Cl.
| | |
|---|---|
| *A61K 38/47* | (2006.01) |
| *A61K 45/06* | (2006.01) |
| *A61K 38/12* | (2006.01) |
| *A61K 38/14* | (2006.01) |
| *C12N 9/36* | (2006.01) |
| *C12N 9/80* | (2006.01) |

(52) U.S. Cl.
CPC .............. *A61K 38/47* (2013.01); *A61K 38/12* (2013.01); *A61K 38/14* (2013.01); *A61K 45/06* (2013.01); *C12N 9/2462* (2013.01); *C12N 9/80* (2013.01); *C12Y 305/01028* (2013.01)

(58) Field of Classification Search
None
See application file for complete search history.

(56) References Cited

FOREIGN PATENT DOCUMENTS

WO 2009/035303 * 3/2009

OTHER PUBLICATIONS

Abedon, S.T. (2011) "*Lysis from Without*," Bacteriophage 1(1):46-49.
Atilano, M.L. et al. (2010) "*Teichoic Acids are Temporal and Spatial Regulators of Peptidoglycan Cross-Linking in Staphylococcus aureus*," Proc. Nat'l. Acad. Sci. U.S.A. 107(44): 18991-18996.
Bateman, A. et al. (2003)"*The CHAP Domain: A Large Family of Amidases Including GSP Amidase and Peptidoglycan Hydrolases*," Trends Biochem. Sci. 28(5):234-237.
Becker, S.C. et al. (2008) "*The Phage K Lytic Enzyme LysK and Lysostaphin Act Synergistically to Kill MRSA*," FEMS Microbiol. Lett. 287(2):185-191.
Becker, S.C. et al. (2009) "*LysK CHAP Endopeptidase Domain is Required for Lysis of Live Staphylococcal Cells*," FEMS Microbiol. Lett. 294(1): 52-60.
Borysowski, J. et al. (2011) "*Potential of Bacteriophages and Their Lysins in the Treatment of MRSA: Current Status and Future Perspectives*," BioDrugs 25(6):347-355.
CDC (2013) "*Antibiotic resistance threats in the United States, 2013*," Centers for Disease Control and Prevention, Atlanta.
Celia, L.K. et al. (2008) "*Characterization of a Bacteriophage Lysin (Ply700) from Streptococcus Uberis*," Vet Microbiol. 130(1-2):107-117.
Danner, M. et al. (1993) "*Folding and Assembly of Phage P22 Tailspike Endorhamnosidase Lacking the N-terminal, Head-binding Domain*," Eur. J. Biochem. 215(3):653-661.
Davis, K.M. et al. (2011) "*Modifications to the Peptidoglycan Backbone Help Bacteria to Establish Infection*," Infect. Immun. 79(2):562-570.
Donovan, D.M. et al. (2006) "*Lysis of Staphylococcal Mastitis Pathogens by Bacteriophage Phi11 Endolysin*," FEMS Microbiol. Lett. 265(1):133-139.
Ekici, O.D. et al. (2008) "*Unconventional Serine Proteases: Variations of the Catalytic Ser/His/Asp Triad Configuration*," Protein Science: A Publication of the Protein Society 17(12):2023-2037.
Fallas, J.A. et al. (2012) "*Computational Design of Self-assembling Register-specific Collagen Heterotrimers*," Nat. Commun. 3(1087):1-8.
Fenton, M. et al. (2011) "*Characterization of the Staphylococcal Bacteriophage Lysin CHAP(K)*," J. Appl. Microbiol. 111(4):1025-1035.
Filatova, L.Y. et al. (2010) "*LysK, the Enzyme Lysing Staphylococcus aureus Cells: Specific Kinetic Features and Approaches Towards Stabilization*," Biochimie 92(5):507-513.
Fischetti, V.A. (2005) "*Bacteriophage Lytic Enzymes: Novel Anti-infectives*," Trends Microbiol. 13(10):491-496.
Garcia, P. et al. (2010) "*Synergy Between the Phage Endolysin LysH5 and Nisin to Kill Staphylococcus aureus in Pasteurized Milk*," Int. J. Food Microbiol. 141(3):151-155.
Gilmer, D.B. et al. (2013) "*Novel Bacteriophage Lysin with Broad Lytic Activity Protects Against Mixed Infection by Streptococcus Pyogenes and Methicillin-resistant Staphylococcus aureus*," Antimicrobial Agents and Chemotherapy 57(6):2743-2750.
Gu, J. et al. (2014) "*Structural and Biochemical Characterization Reveals LysGH15 as an Unprecedented "EF-Hand-like" Calcium-binding Phage Lysin*," PLoS Pathogens 10(5):e1004109.
Howden, B.P. et al. (2010) "*Reduced Vancomycin Susceptibility in Staphylococcus aureus, Including Vancomycin-intermediate and Heterogeneous Vancomysin-intermediate Strains: Resistance Mechanisms, Laboratory Detection, and Clinical Implications*," Clin. Microbiol. Rev. 23(1):99-139.
Huang, S.S. et al. (2013) "*Targeted Versus Universal Decolonization to Prevent ICU Infection*," N. Engl. J. Med. 368(24):2255-2265.
Jun, S.Y. et al. (2011) "*Comparison of the Antibacterial Properties of Phage Endolysins SAL-1 and LysK*," Antimicrobial Agents and Chemotherapy 55(4):1764-1767.

(Continued)

*Primary Examiner* — Patricia Duffy
(74) *Attorney, Agent, or Firm* — William C. Schrot; AuerbachSchrot LLC

(57) ABSTRACT

The present invention relates to methods of treating or preventing a bacterial disease or infection, antibacterial compositions, and antibacterial surfaces, including isolated endolysin polypeptides from bacteriophage GRCS.

8 Claims, 7 Drawing Sheets

(56) References Cited

OTHER PUBLICATIONS

Khayat, R. et al. (2001) "*Investigating the Role of Histidine 157 in the Catalytic Activity of Human Cytomegalovirus Protease*," Biochemistry 40(21):6344-6351.

Kusuma, C.M. et al. (2005) "*Comparison of Four Methods for Determining Lysostaphin Susceptibility of Various Strains of Staphylococcus aureus*," Antimicrobial Agents and Chemotherapy 49(8):3256-3263.

Linden et al. (2014) "*Biochemical and biophysical characterization of PlyGRCS, a bacteriophage endolysin active against methicillin-resistant Staphylococcus aureus*," Appl. Microbiol. Biotechnol. 99:741-752.

Loeffler, J.M. et al. (2003) "*Synergistic Lethal Effect of a Combination of Phage Lytic Enzymes with Different Activities on Penicillin-sensitive and—resistant Streptococcus Pneumoniae Strains*," Antimicrobial Agents and Chemotherapy 47(1): 375-377.

Low, L.Y. et al. (2011) "*Role of Net Charge on Catalytic Domain and Influence of Cell Wall Binding Domain on Bactericidal Activity, Specificity, and Host Range of Phage Lysins*," J. Biol. Chem. 286(39):34391-34403.

Lowy, F.D. (1998) "*Staphylococcus aureus Infections*," N. Engl. J. Med. 339(8):520-532.

McGowan, S. et al. (2012) "*X-ray Crystal Structure of the Streptococcal Specific Phage Lysin PlyC*," Proc. Nat'l. Acad. Sci. U.S.A. 109(31):12752-12757.

Micek, S.T. (2007) "*Alternatives to Vancomycin for the Treatment of Methicillin-resistant Staphylococcus aureus Infections*," Clinical Infectious Diseases: An Official Publication of the Infectious Diseases Society of America 45 Suppl 3:S184-S190.

Mokrasch, L. (1967) "*Use of 2, 4, 6-trinitrobenzenesulfonic Acid for the Coestimation of Amines, Amino Acids, and Proteins in Mixtures*," Anal. Biochem. 18:64-71.

Nelson, D.C. et al. (2012) "*Endolysins as Antimicrobials*," Adv. Virus. Res. 83:299-365.

Pritchard, D.G. et al. (2004) "*The Bifunctional Peptidoglycan Lysin of Streptococcus Agalactiae Bacteriophage B30*," Microbiology 150(Pt 7):2079-2087.

Rigden, D.J. et al. (2003) "*Amidase Domains from Bacterial and Phage Autolysins Define a Family of Gamma-D, L-glutamate-specific Amidohydrolases*," Trends Biochem. Sci. 28(5):230-234.

Romero-Vivas et al. (1995) "*Mortality associated with nosocomial bacteremia due to methicillin-resistant Staphylococcus aureus*," Clin. Infect. Dis. 21(6):1417-1423.

Sanz, J.M. et al. (1993) "*Thermal Stability and Cooperative Domains of CPL1 Lysozyme and Its NH2- and COOH-terminal Modules*," J. Biol. Chem. 268(9):6125-6130.

Sass, P. et al. (2007) "*Lytic Activity of Recombinant Bacteriophage Phi11 and Phi12 Endolysins on Whole Cells and Biofilms of Staphylococcus aureus*," Appl. Environ. Microbiol. 73(1): 347-352.

Schmelcher et al. (2011) "*Domain shuffling and module engineering of Listeria phage endolysins for enhanced lytic activity and binding affinity*," Microb. Biotechnol. 4(5):651-662.

Schmelcher, M. et al. (2012) "*Bacteriophage Endolysins as Novel Antimicrobials*," Future Microbiol. 7(10):1147-1171.

Schmelcher, M. et al. (2012) "*Chimeric Phage Lysins Act Synergistically with Lysostaphin to Kill Mastitis-causing Staphylococcus aureus in Murine Mammary Glands*," Appl. Environ. Microbiol. 78(7):2297-2305.

Schmelcher, M. et al. (2012) "*Listeria Bacteriophage Peptidoglycan Hydrolases Feature High Termoresistance and Reveal Increased Activity After Divalent Metal Cation Substitutions*," Appl. Microbiol. Biotechnol. 93(2):633-643.

Schuch, R. et al. (2002) "*A Bacteriolytic Agent That Detects and Kills Bacillus Anthracis*," Nature 418(6900):884-889.

Schuch, R. et al. (2013) "*Combination Therapy with Lysin CF-301 and Antibiotic is Superior to Antibiotic Alone for Treating Methicillin-resistant Staphylococcus aureus-induced Murine Bacteremia*," J. Infect. Dis. 209:1469-1478.

Shen, Y. et al. (2012) "*Phage-based Enzybiotics*," Adv. Mol. Biol. 24:217-239.

Sieradzki, K. et al. (2003) "*Alterations of Cell Wall Structure and Metabolism Accompany Reduced Susceptibility to Vancomycin in an Isogenic Series of Clinical Isolates of Staphylococcus aureus*," J. Bacteriol. 185(24):7103-7110.

Son, B. et al. (2012) *Characterization of LysB4, an Endolysin From the Bacillus Cereus-infecting Bacteriophage B4*,: BMC Microbiol. 12:33.

Spratt, B.G. (1994) "*Resistance to Antibiotics Mediated by Target Alterations*," Science 264(5157):388-393.

Sunagar, R. et al. (2010) "*Bacteriophage Therapy for Staphylococcus aureus Bacteremia in Streptozotocin-induced Diabetic Mice*," Res. Microbiol. 161(10):854-860.

Swift, S.M. et al. (2014) "*Complete Genome Sequence of Staphylococcus aureus Phage GRCS*," Genome Announc. 2(2):e0020914.

Tang, Y.W. et al. (2010) "*Staphylococcus aureus: An Old Pathogen with New Weapons*," Clin. Lab. Med. 30(1):179-208.

Taubes, G. (2008) "*The Bacteria Fight Back*," Science 321(5887):356-361.

Vollmer, W. (2008) "*Structural Variation in the Glycan Strands of Bacterial Peptidoglycan*," FEMS Microbiol. Rev. 32(2):287-306.

Weidenmaier, C. et al. (2004) "*Role of Teichoic Acids in Staphylococcus aureus Nasal Colonization, a Major Risk Factor in Nosocomial Infections*," Nat. Med. 10(3):243-245.

Whitmore, L. et al. (2004) "*DICHROWEB, an Online Server for Protein Secondary Structure Analyses From Circular Dichroism Spectroscopic Data*," Nucleic Acids Res. 32:W668-W673.

Gebart et al. (2012) "Novel High-Molecule Weight, R-Type Bacteriocins of Clostridium difficile," J. Bacteriology 194(22):6240-6247.

Parmley, S. (2014) "Lysin in Wait," Targets & Mechanisms, SciBX:Science-Business eXchange.

Szweda et al. (2012) "Peptidoglycan hydrolases-potential weapons," Appl. Microbiol. Biotechnol. 96:1157-1174.

Thummeepak et al. (2016) "Enhanced Antibacterial Activity of Acinetobacter baumannii Bacteriophage ØABP-01 Endolysin (LysABP-01) in Combination with Colistin," Frontiers in Microbiology, vol. 7, Article 1402.

\* cited by examiner

A.

B.

C.

D.

C.

ENDOLYSINS ACTIVE AGAINST *STAPHYLOCOCCUS* BACTERIA, PHARMACEUTICAL COMPOSITIONS, AND METHODS RELATING THERETO

CROSS-REFERENCE TO RELATED APPLICATIONS

This application is based on U.S. Provisional Patent Application Ser. No. 62/023,096, filed Jul. 10, 2014, which application is incorporated herein by reference in its entirety and to which priority is claimed.

STATEMENT REGARDING FEDERALLY SPONSORED RESEARCH OR DEVELOPMENT

This work was supported by the U.S. Department of Defense as provided for by the terms of Contract No. W81XWH1120006 (Grant No. DM102823). The U.S. government has certain rights in this invention.

REFERENCE TO SEQUENCE LISTING

This application includes one or more Sequence Listings pursuant to 37 C.F.R. 1.821 et seq., which are disclosed in computer-readable media (file name: 2105_0062C_SUB_SeqList_ST25.txt, created Oct. 21, 2015, and having a size of 10715 bytes), which file is herein incorporated by reference in its entirety.

FIELD OF THE INVENTION

The present invention relates to methods of treating or preventing bacterial infection, antibacterial compositions, and devices including antibacterial surfaces, incorporating isolated endolysin polypeptides from bacteriophage GRCS.

BACKGROUND OF THE INVENTION

It has been estimated that 70% of the bacteria that cause hospital-acquired infections are now resistant to one or more antibiotics (Taubes G (2008) *The bacteria fight back*. Science 321(5887):356-61). One of the most alarming antibiotic-resistant bacterial species is *Staphylococcus aureus*. Specifically, methicillin-resistant *S. aureus* (MRSA) are the group of *S. aureus* strains resistant to the entire class of β-lactam antibiotics. Hospital-acquired MRSA (HA-MRSA) often leads to severe and life-threatening infections, such as those at surgical sites, in the bloodstream, or pneumonia, while community-acquired MRSA (CA-MRSA) typically leads to superficial skin infections that can ultimately progress to induce severe invasive complications, such as necrotizing fasciitis (Lowy F D (1998) *Staphylococcus aureus infections*. N Engl J Med 339(8):520-32; Tang Y W & Stratton C W (2010) *Staphylococcus aureus: An old pathogen with new weapons*. Clin Lab Med 30(1):179-208). In some cases, individuals have died within two days of infection due to the ineffectiveness of present-day antibiotics (Romero-Vivas et al. (1995) *Mortality associated with nosocomial bacteremia due to methicillin-resistant Staphylococcus aureus*. Clin Infect Dis 21(6):1417-23).

Approval of new antibiotics, including linezolid (oxazolidinone class) in 2000, daptomycin (cyclic lipopeptide class) in 2003, and tigecycline (glycylcycline class) in 2005, provides alternatives to vancomycin, which was formerly the only antibiotic treatment for MRSA (Micek S T (2007) *Alternatives to vancomycin for the treatment of methicillin-resistant Staphylococcus aureus infections*. Clinical infectious diseases: an official publication of the Infectious Diseases Society of America 45 Suppl 3:S184-90). These new antibiotics, along with increased awareness and adherence to universal decolonization practices, have led to a decrease in the incidence of MRSA in intensive care units (Huang S S et al. (2013) *Targeted versus universal decolonization to prevent ICU infection*. N Engl J Med 368(24):2255-65). Nonetheless, a recent report from the Centers for Disease Control and Prevention indicates there are still over 80,000 severe MRSA infections per year in the United States, resulting in over 11,000 deaths (e.g., see CDC (2013) *Antibiotic resistance threats in the United States, 2013*. Centers for Disease Control and Prevention, Atlanta). The same CDC report labeled MRSA as a "serious" public health threat, and vancomycin-resistant *S. aureus* (VRSA) as a "concerning" threat, underscoring the need for development of alternative therapeutics.

To counteract bacterial resistance and ameliorate the problems caused by *S. aureus* infections, endolysin therapy is one avenue that is being pursued (Borysowski J et al. (2011) *Potential of bacteriophages and their lysins in the treatment of MRSA: current status and future perspectives*. BioDrugs 25(6):347-55; Nelson D C et al. (2012) *Endolysins as antimicrobials*. Adv Virus Res 83:299-365). Endolysins are enzymes released by bacteriophages during the lytic cycle of viral infection. A lytic enzyme is capable of specifically cleaving bonds that are present in the peptidoglycan of bacterial cells to disrupt the bacterial cell wall. The bacterial cell wall peptidoglycan is highly conserved among most bacteria, and cleavage of only a few bonds is believed to disrupt the bacterial cell wall. Once produced within the bacterial cytoplasm by replicating bacteriophage, endolysins hydrolyze bonds in the bacterial cell wall (i.e. peptidoglycan) until lysis is complete.

The idea of utilizing endolysins therapeutically is based on the phenomenon of "lysis from without", a phrase used to describe the destruction of the bacterial envelope without production of phage virions (Abedon S T (2011) *Lysis from without*. Bacteriophage 1(1):46-49). This phenomenon only occurs in Gram-positive organisms, such as MRSA, because such bacteria lack an outer membrane protecting the cell wall (Schmelcher et al. (2011) *Domain shuffling and module engineering of Listeria phage endolysins for enhanced lytic activity and binding affinity*. Microb Biotechnol 4(5):651-62). Rather, the cell wall of such Gram-positive bacteria includes interconnecting layers consisting primarily of peptidoglycan. Gram-positive bacteria include, inter alia, numerous species within the genera *Actinomyces, Bacillus, Listeria, Lactococcus, Staphylococcus, Streptococcus, Enterococcus, Mycobacterium, Corynebacterium,* and *Clostridium*.

The classical structure of endolysins that act on Gram-positive cell walls employs a modular architecture consisting of an N-terminal catalytic domain linked to a C-terminal cell wall binding domain (CBD). The catalytic domain is responsible for cleaving specific covalent bonds in the peptidoglycan structure that are essential for maintaining its intrinsic structural integrity. The CBD confers endolysin specificity by recognizing and noncovalent binding to species- or strain-specific epitopes associated with the cell envelope. It is the high specificity derived by the combined actions of the catalytic and CBD domains that cause endolysins to be highly refractory to the resistance commonly observed upon treatment with classical antibiotics (Fischetti V A (2005) *Bacteriophage lytic enzymes: novel anti-infectives*. Trends Microbiol 13(10):491-6; Schuch R et al. (2002)

*A bacteriolytic agent that detects and kills Bacillus anthracis*. Nature 418(6900):884-9). This is due to the evolution of bacteriophage to target specific, conserved bonds in the peptidoglycan of a bacteria cell wall, ensuring that the progeny phage will survive (Low L Y et al. (2011) *Role of net charge on catalytic domain and influence of cell wall binding domain on bactericidal activity, specificity, and host range of phage lysins*. J Biol Chem 286(39):34391-403). However, if resistance were to develop, endolysins could be engineered through domain shuffling or used in combination with other endolysins or antibiotics to prolong the use of these enzymes (Shen Y et al. (2012) *Phage-based Enzybiotics*. In: Abedon S, Hyman P (eds) Bacteriophages in Health and Disease. CABI Press, pp 217-239).

Thus, identified endolysins have been shown to be effective in killing specific bacterial strains. However, there still exists a need for additional and/or alternative endolysin-based therapeutics, particularly therapeutics exhibiting superior activity and/or which target other bacterial strains as compared to known therapeutics.

SUMMARY OF THE INVENTION

The increasing rate of resistance of pathogenic bacteria, such as *S. aureus*, to classical antibiotics has driven research towards identification of other means to fight infectious diseases. The present invention relates to methods of treating such infectious diseases by administering to a subject a therapeutically effective amount of particular bacteriophage-encoded peptidoglycan hydrolase, called endolysin(s) or enzybiotic(s). The endolysin polypeptides of the present invention lyse the bacterial cell wall upon direct contact, are not inhibited by traditional antibiotic resistance mechanisms, and thus are suitable for numerous applications, e.g., such as in the areas of food safety, human health, and veterinary science.

In particular, the present invention is directed to methods, compositions and devices incorporating or utilizing particular endolysin polypeptide(s) from the bacteriophage GRCS, sometimes referred to herein as PlyGRCS endolysin or endolysin polypeptide (which have the disclosed amino acid sequences, variants thereof, or active fragments thereof). According to disclosed embodiments, PlyGRCS endolysin(s) are utilized for treating infectious disease associated with Gram-positive bacteria, in particular *Staphylococcus* bacteria (e.g., *S. aureus* and *S. epidermidis*) including methicillin- and vancomycin-resistant strains (e.g., methicillin-resistant *S. aureus* (MRSA), vancomycin-intermediate-resistant *S. aureus* (VISA), and methicillin-resistant *S. epidermidis*).

Thus, one aspect of the present invention provides for endolysin polypeptides having killing activity against gram-positive bacteria, particularly *Staphylococcus* bacteria. In accordance with disclosed embodiments, a method of killing gram-positive bacteria is provided by contacting bacteria with a composition comprising an amount of isolated endolysin polypeptide effective to kill such bacteria, the isolated endolysin polypeptide comprising an amino acid sequence of SEQ ID NOs: 5, 6 and/or 7 or variants thereof.

Another aspect of the present invention relates to methods of treating bacterial infection (e.g., an infection or disease caused by a *Staphylococcus* species such as *S. aureus*) in a subject (e.g., a human patient) comprising administering to the patient a therapeutically effective amount of an isolated endolysin polypeptide comprising the amino acid sequence of SEQ ID NOs: 5, 6 and/or 7, or variants thereof having at least 80% identity thereto. In some embodiments, the method includes the further step of administering to the subject a secondary therapeutic agent (e.g., one or more antibiotic) after or concurrent with the administration of the isolated polypeptide.

The present invention also relates to pharmaceutical compositions for killing Gram-positive bacteria comprising an isolated polypeptide comprising the amino acid sequence of SEQ ID NOs: 5, 6 and/or 7, or variants thereof having at least 80% identity thereto, and a pharmaceutically acceptable carrier. In some embodiments, the pharmaceutical composition further comprises one or more antibiotic, such as for example a penicillin, a cephalosporin, a polymyxin, an ansamycin, a quinolone, a sulfonamide, a lipopeptide, a glycycline, and/or an oxazolidinone. In some implementations, the antibiotic is selected from the group consisting of linezolid, daptomycin, and tigecycline, vancomycin, fidaxomicin, and metronidazole.

The present invention is also directed to a substrate (e.g., such as a device or apparatus, such as a medical instrument or device or an implantable medical device) including a surface comprising an antibacterial coating or material coupled thereto, wherein the coating or material comprises an isolated polypeptide comprising the amino acid sequence of SEQ ID NOs: 5, 6 and/or 7, or variants thereof having at least 80% identity thereto. In some implementations, the coating or material comprises one or more secondary therapeutic agent(s), such as for example an antimicrobial or an antibiotic (e.g., a penicillin, a cephalosporin, a polymyxin, an ansamycin, a quinolone, a sulfonamide, a lipopeptide, a glycycline, and an oxazolidinone).

BRIEF DESCRIPTION OF THE DRAWINGS

As shown in FIG. 6, Plate A, ESI-MS analysis of PlyGRCS digested peptidoglycan results in a spectrum (top) containing a peak at m/z=702.35, indicating that PlyGRCS possesses endopeptidase and amidase activities. This peak is absent in peptidoglycan digested with a known N-acetylmuramoyl-L-alanine amidase (second spectrum), or undigested peptidoglycan (third spectrum). Double digest with PlyGRCS and CHAP-K (bottom spectrum) yields a spectrum identical to that of PlyGRCS alone. FIG. 6, Plate B, shows schematically the $A_2QKG_5$ fragment corresponding to the 702.35 peak generated by both an N-acetylmuramoyl-L-alanine amidase activity (black arrows) and a D-alanyl-glycyl endopeptidase activity (white arrows). As shown in FIG. 6, Plate C, PlyGRCS peptidoglycan digest data shows both the $A_2QKG_5$ (702.35 m/z peak) and the larger, doubly charged $A_4Q2K_2G_{10}$ moiety (684.84 m/z peak).

DETAILED DESCRIPTION OF EMBODIMENTS OF THE INVENTION

Figure 1:
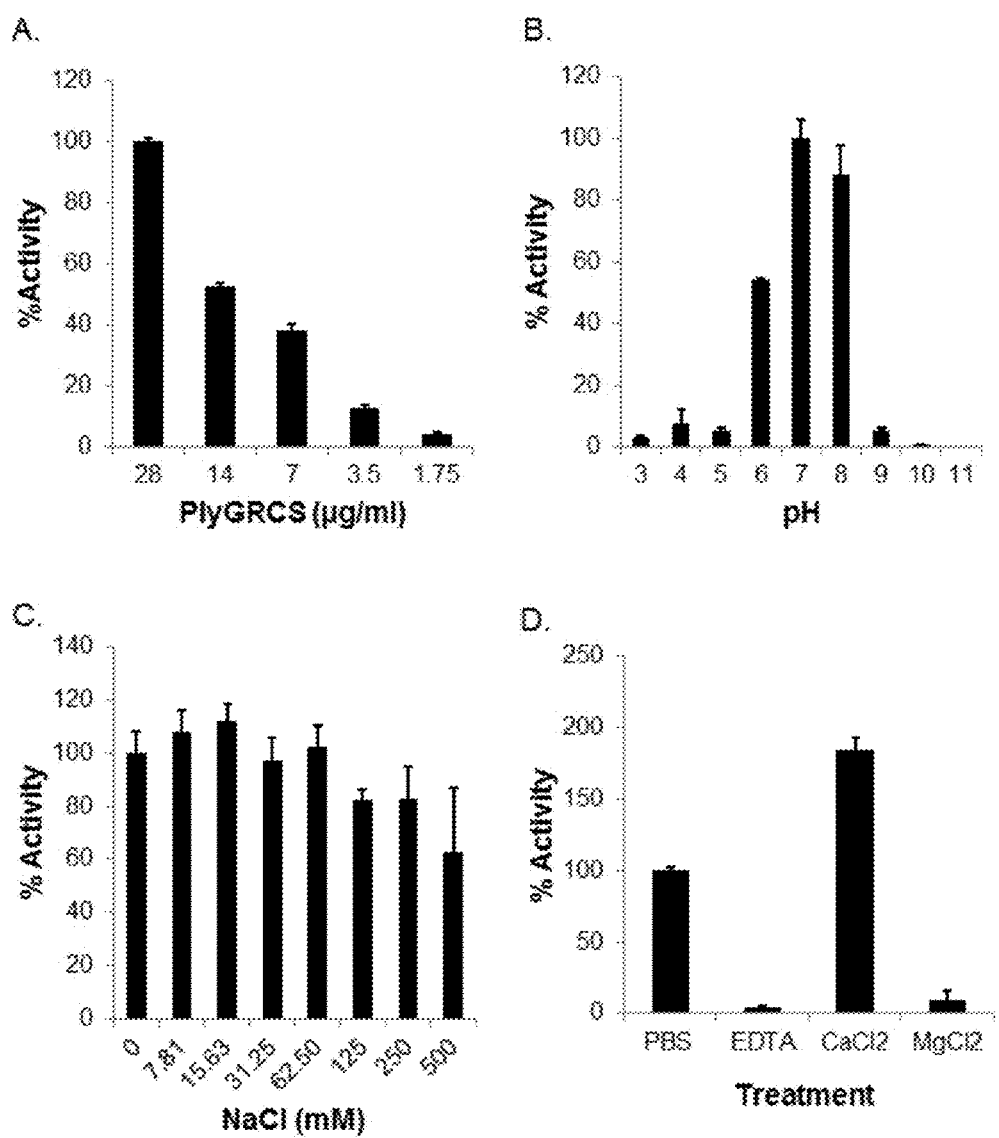
FIG. 1 illustrates biochemical characterization of optimal conditions for PlyGRCS activity. The influence of dose (FIG. 1, Plate A), pH (FIG. 1, Plate B), NaCl (FIG. 1, Plate C), and divalent cations (FIG. 1, Plate D) on PlyGRCS activity against stationary phase *S. aureus* NRS-14 are shown. Error bars represent the standard deviation, and all experiments were done in triplicate.

Embodiments of the present invention relate to compositions, methods and devices for preventing or treating disease or infection associated with or caused by gram-positive bacteria, such compositions, methods and devices incorporating and/or utilizing isolated endolysin polypeptide(s) from the GRCS bacteriophase (Sunagar R et al. (2010) *Bacteriophage therapy for Staphylococcus aureus bacteremia in streptozotocin-induced diabetic mice*. Res Microbiol 161(10):854-60). As used herein, an "isolated" endolysin polypeptide(s) or nucleic acid encoding such polypeptide(s) are free or substantially free of material with which they are naturally associated such as other polypeptides or nucleic acids. Polypeptides and nucleic acid may be formulated or mixed with pharmaceutically acceptable carriers, diluents or adjuvants (e.g., such as in pharmaceutical compositions and/or when used in methods of treatment or therapy) and still be isolated.

The PlyGRCS endolysin(s) of the present invention displays dose-dependent antimicrobial activity against both planktonic and biofilm *S. aureus*, including MRSA. The host range for this enzyme includes all *S. aureus* and *S. epidermidis* strains tested. In some implementations, compositions and methods including PlyGRCS endolysin(s) exhibit activity against *S. aureus* and *S. epidermidis* strains, but not against other Gram-positive pathogens.

PlyGRCS contains an N-terminal cysteine, histidine-dependent amidohydrolase/peptidase (CHAP) catalytic domain and a C-terminal bacterial src-homology 3 (SH3_5) binding domain. The endolysin polypeptide(s) of the present invention may be isolated from the GRCS bacteriophage, or prepared by recombinant or synthetic methods as known in the art. Nucleic acid and amino acid sequences of embodiments of the present invention are presented below:

PlyGRCS Native DNA Sequence (unoptimized) (SEQ ID NO: 1):

ATGAAATCACAACAACaAGCaAAAGAATGGATATATAAACATGAGGGTAC

TgGTGTTgACTTTGATGGTGCATATgGtTTTCAATGTATGGAcTTAGCtg

TTGctTaTgTATAtTACATTACAGACGGTAAAGTTCGTATGTgGGGTAAC

GCCAAAGACGCTATTAATAATGACTTTAAAGGTTTAGCAACGGTGTATGA

AAATACACCGAGCTTTAAACCTCAATTAGGTGACGTTGCTGTTTATACTA

ATTCTCAATATGGTCACATTCAATGTGTaATAAGTGGTAATTTAGATTAT

TATACATGtTTAGAGCaAAACTGGTTAGGTGGTGGGTTTGACGGTTGGGa aAAAGCAACAATAAGAACACATTATTATGACGGTGTAACACACTTTATTA

GACCtAAATTTTcTGCTAGTAATAGTAATGTATTAGAAACATCAAAAGTA

AATaCATTTGGAAATTGGaAACaAAACCAATACGGAACATATTACAGAAA

TGAAAATgcAACATTTACATGTGGAtTTTTACCAATATTTGCACGTGTaG

GTAGTcCTAAAtTAAGTGAAcCTAATgGATAtTgGtTcCaAcCaAATGGT

TATACAcCATAtgACGAAGTTTGTTTATCAGATGGACTAgTGTGGATTgG

TTATAATTGGCAAgGaACACGTTAttatttaccagtgaGACAATGGAACG

GTAAAACGGGTAATAGTTATAGCATTGGTTTACCCTGGGGGTGTTCTCA

TAA

PlyGRCS Native DNA Sequence (unoptimized; including 6x His tag (underlined) added at the C-terminus) (SEQ ID NO: 2):

ATGAAATCACAACAACaAGCaAAAGAATGGATATATAAACATGAGGGTAC

TgGTGTTgACTTTGATGGTGCATATgGtTTTCAATGTATGGAcTTAGCtg

TTGctTaTgTATAtTACATTACAGACGGTAAAGTTCGTATGTgGGGTAAC

GCCAAAGACGCTATTAATAATGACTTTAAAGGTTTAGCAACGGTGTATGA

AAATACACCGAGCTTTAAACCTCAATTAGGTGACGTTGCTGTTTATACTA

ATTCTCAATATGGTCACATTCAATGTGTaATAAGTGGTAATTTAGATTAT

TATACATGtTTAGAGCaAAACTGGTTAGGTGGTGGGTTTGACGGTTGGGa aAAAGCAACAATAAGAACACATTATTATGACGGTGTAACACACTTTATTA

GACCtAAATTTTcTGCTAGTAATAGTAATGTATTAGAAACATCAAAAGTA

AATaCATTTGGAAATTGGaAACaAAACCAATACGGAACATATTACAGAAA

TGAAAATgcAACATTTACATGTGGAtTTTTACCAATATTTGCACGTGTaG

GTAGTcCTAAAtTAAGTGAAcCTAATgGATAtTgGtTcCaAcCaAATGGT

TATACAcCATAtgACGAAGTTTGTTTATCAGATGGACTAgTGTGGATTgG

TTATAATTGGCAAgGaACACGTTAttatttaccagtgaGACAATGGAACG

GTAAAACGGGTAATAGTTATAGCATTGGTTTACCCTGGGGGTGTTCTCA

CATCATCATCATCATCATTAA

PlyGRCS Codon Optimized DNA Sequence (75% similarity to native DNA sequence) (SEQ ID NO: 3):

ATGAAATCACAGCAGCAGGCTAAAGAATGGATTTATAAACATGAAGGAAC

TGGTGTTGATTTCGACGGCGCTTACGGGTTTCAGTGTATGGACCTGGCCG

TGGCGTATGTGTACTATATTACCGACGGGAAAGTCCGTATGTGGGGTAAT

GCGAAGGATGCGATTAATAACGATTTTAAAGGCTTAGCCACGGTCTATGA

AAATACTCCGTCATTTAAGCCGCAGCTGGGGGACGTGGCCGTATATACGA

ACAGCCAGTATGGGCATATCCAGTGCGTGATTAGCGGAAATCTGGACTAC

TACACGTGCCTTGAACAGAACTGGCTCGGGGGAGGGTTCGACGGTTGGGA

-continued

```
AAAAGCGACTATCCGTACCCATTATTACGATGGAGTGACCCATTTTATTC

GTCCGAAGTTTAGTGCTTCTAACAGCAATGTTCTGGAAACTAGCAAGGTG

AATACTTTTGGAAACTGGAAACAGAATCAGTACGGCACGTATTATCGGAA

TGAGAACGCCACTTTCACGTGTGGTTTCCTGCCGATTTTCGCTCGTGTCG

GCTCGCCTAAATTGTCCGAACCGAACGGCTATTGGTTCCAGCCGAATGGT

TATACCCCGTATGATGAGGTGTGCTTGTCCGACGGTCTGGTGTGGATCGG

TTACAACTGGCAGGGAACCCGTTACTACCTTCCGGTGCGTCAGTGGAATG

GCAAAACGGGGAATTCTTACTCTATTGGACTTCCATGGGCGTTTTTTCA

TAA
```

PlyGRCS Codon Optimized DNA Sequence (75% similarity to native DNA sequence; 6x His tag added at the C-terminus) (SEQ ID NO: 4):

```
ATGAAATCACAGCAGCAGGCTAAAGAATGGATTTATAAACATGAAGGAAC

TGGTGTTGATTTCGACGGCGCTTACGGGTTTCAGTGTATGGACCTGGCCG

TGGCGTATGTGTACTATATTACCGACGGGAAAGTCCGTATGTGGGGTAAT

GCGAAGGATGCGATTAATAACGATTTTAAAGGCTTAGCCACGGTCTATGA

AAATACTCCGTCATTTAAGCCGCAGCTGGGGGACGTGGCCGTATATACGA

ACAGCCAGTATGGGCATATCCAGTGCGTGATTAGCGGAAATCTGGACTAC

TACACGTGCCTTGAACAGAACTGGCTCGGGGGAGGGTTCGACGGTTGGGA

AAAAGCGACTATCCGTACCCATTATTACGATGGAGTGACCCATTTTATTC

GTCCGAAGTTTAGTGCTTCTAACAGCAATGTTCTGGAAACTAGCAAGGTG

AATACTTTTGGAAACTGGAAACAGAATCAGTACGGCACGTATTATCGGAA

TGAGAACGCCACTTTCACGTGTGGTTTCCTGCCGATTTTCGCTCGTGTCG

GCTCGCCTAAATTGTCCGAACCGAACGGCTATTGGTTCCAGCCGAATGGT

TATACCCCGTATGATGAGGTGTGCTTGTCCGACGGTCTGGTGTGGATCGG

TTACAACTGGCAGGGAACCCGTTACTACCTTCCGGTGCGTCAGTGGAATG

GCAAAACGGGGAATTCTTACTCTATTGGACTTCCATGGGCGTTTTTTCA

CACCACCACCACCATCATTAA
```

PlyGRCS Protein Sequence (amino acids 1-250) (SEQ ID NO: 5):

```
MKSQQQAKEWIYKHEGTGVDFDGAYGFQCMDLAVAYVYYITDGKVRMWGN

AKDAINNDFKGLATVYENTPSFKPQLGDVAVYTNSQYGHIQCVISGNLDY

YTCLEQNWLGGGFDGWEKATIRTHYYDGVTHFIRPKFSASNSNVLETSKV

NTFGNWKQNQYGTYYRNENATFTCGFLPIFARVGSPKLSEPNGYWFQPNG

YTPYDEVCLSDGLVWIGYNWQGTRYYLPVRQWNGKTGNSYSIGLPWGVFS
```

PlyGRCS Catalytic Domain (CHAP$_{GRCS}$, amino acids 1-140) (SEQ ID NO: 6):

```
MKSQQQAKEWIYKHEGTGVDFDGAYGFQCMDLAVAYVYYITDGKVRMWGN

AKDAINNDFKGLATVYENTPSFKPQLGDVAVYTNSQYGHIQCVISGNLDY

YTCLEQNWLGGGFDGWEKATIRTHYYDGVTHFIRPKFSAS
```

PlyGRCS Binding Domain (SH3_5$_{GRCS}$, amino acids 150-250) (SEQ ID NO: 7):

```
NTFGNWKQNQYGTYYRNENATFTCGFLPIFARVGSPKLSEPNGYWFQPNG

YTPYDEVCLSDGLVWIGYNWQGTRYYLPVRQWNGKTGNSYSIGLPWGVFS
```

A "polypeptide" includes a polymer molecule comprised of multiple amino acid residues joined in a linear manner. The polypeptide may include conservative substitutions where the naturally occurring amino acid(s) is replaced by one having similar properties, where such conservative substitutions do not alter the function of the polypeptide.

The disclosed endolysin polypeptides may be engineered through domain shuffling or used in combination with other endolysins or antibiotics to prolong therapeutic efficacy (Shen Y et al. (2012) Phage-based Enzybiotics. In: Abedon S, Hyman P (eds) Bacteriophages in Health and Disease. CABI Press, pp 217-239). Endolysin polypeptides of the present invention may be truncated, chimeric, shuffled or natural (e.g., corresponding to wild-type). A "chimeric" polypeptide may be produced by combining two or more proteins having two or more active sites. Chimeric polypeptides may act independently on the same or different molecules, and hence may potentially exhibit activity against two or more different bacterial species or antigen targets.

In accordance with some embodiments, polypeptides are prepared or engineered to exhibit amino acid sequence percent identity of at least 60%, 70%, 80%, 85%, and preferably at least 90%, 95%, 98% or 99% percent identity, with active regions of PlyGRCS endolysin, including in SEQ ID NOs: 5, 6 and/or 7, and also exhibiting functionality and/or comparable therapeutic efficacy (e.g., bacterial effects) therewith. Amino acid sequence percent identity is defined as the percentage of amino acid residues in a candidate sequence that are identical with the amino acid residues in the wild-type bacteriophage associated PlyGRCS endolysin sequence, after aligning the sequences in the same reading frame and introducing gaps, if necessary, to achieve the maximum percent sequence identity, and not considering any conservative substitutions as part of the sequence identity.

Mutations can be made in the disclosed amino acid sequences, or in the nucleic acid sequences encoding the polypeptides herein, or in active fragments or truncations thereof, such that a particular codon is modified to a codon which codes for a different amino acid, an amino acid is substituted for another amino acid, or one or more amino acids are deleted. Preferably, any such mutations do not significantly alter the activity of the resulting polypeptide.

Thus, one of skill in the art, based on a review of the disclosed sequences of the PlyGRCS endolysin(s) of the present invention, may implement amino acid mutations in the polypeptide sequences to identify additional variants thereof (e.g., via random mutagenesis or by a site-directed method such as polymerase chain-mediated amplification with primers that encode the mutated locus). Further, mutagenizing entire codons rather than single nucleotides results in a semi-randomized repertoire of amino acid mutations. Libraries can be constructed consisting of a pool of variants each of which differs by a single amino acid alteration and/or which contain variants representing each possible amino acid substitution for each residue. Variants may be screened for desired activity using any screening method known in the art.

Variants may include one or more amino acid mutations (e.g., 1, 1-5, 1-10, or 10 or more) in the sequence of the endolysin polypeptide(s), and also exhibit comparable functionality (e.g., comparable activity against bacteria) to the native endolysin polypeptide. Activity of such variant(s) may be tested using assays and methods as described herein and as known in the art. One of skill in the art may predict suitable amino acid mutations to achieve such variants based on the disclosure herein.

As discussed in further detail below, contributions of the PlyGRCS putative catalytic and cell wall binding domains were investigated through deletion analysis. PlyGRCS contains a putative cysteine, histidine-dependent amidohydrolase/peptidase (CHAP) catalytic domain. The CHAP domain alone displayed reduced (about 10%) activity as compared to the full length protein, thus indicating that while this domain is responsible for catalytic activity, the binding domain may be desirable in some applications for enhanced efficacy. In contrast, the SH3_5 binding domain lacked activity but was shown to interact directly with the staphylococcal cell wall via fluorescent microscopy.

Site-directed mutagenesis studies determined that active-site residues in the CHAP catalytic domain were C29 and H92, with catalytic functionality benefiting from calcium as a co-factor. A decrease in activity was observed, indicating the importance of these two residues and the presence of an active CHAP domain.

Contributions of the putative catalytic and binding domains were investigated through deletion analysis by turbidity reduction assay. The CHAP catalytic domain displayed activity, though reduced and thus indicating advantages of also providing the binding domain for full efficacy as noted above. The binding domain was confirmed by visualization of cell wall interaction via fluorescent microscopy. Further, as determined by biochemical assays and mass spectrometry, PlyGRCS possesses an N-acetylmuramoyl-L-alanine amidase and a D-alanyl-glycyl endopeptidase catalytic mechanism.

Biochemical assays coupled with mass spectrometry analysis determined that PlyGRCS displays both N-acetyl-muramoyl-L-alanine amidase and D-alanyl-glycyl endopeptidase hydrolytic activities despite possessing only a single catalytic domain. Mass spectrometry of *S. aureus* peptidoglycan digested by PlyGRCS showed a predominant peak at m/z=702, representative of dual catalytic activity. The results herein indicate that PlyGRCS is a revolutionary therapeutic option to combat bacterial infections.

PlyGRCS was found to exhibit strong activity against *Staphylococcus* species (e.g., such as *S. aureus* and *S. epidermidis*), and including methicillin- and vancomycin-resistant strains (e.g., methicillin-resistant *S. aureus* (MRSA), vancomycin intermediate-resistant *S. aureus* (VISA), and methicillin-resistant *S. epidermidis*). Thus, the endolysin polypeptides of the present invention were demonstrated to be highly effective in killing, reducing or eliminating bacterial growth and/or population, and thus are suitable for treating or preventing bacterial infection or symptoms associated with such bacteria in a subject (e.g., a human patient).

Compositions and methods utilizing or including the endolysin polypeptide(s) of the present invention are effective in killing or treating gram-positive bacteria in subjects, either alone or in composition with one or more additional therapeutic agents, such as an antimicrobial or an antibiotic (e.g., including but not limited to, a penicillin, a cephalosporin, a polymyxin, an ansamycin, a quinolone, a sulfonamide, a lipopeptide, a glycycline, and an oxazolidinone. In some implementations, compositions or methods of treatment provide for the use of PlyGRCS endolysin(s) in combination with one or more antibiotic selected from linezolid, daptomycin, tigecycline, vancomycin, fidaxomicin, and/or metronidazole. In some implementations, the endolysin polypeptide(s) of the present invention, or therapeutically active variants thereof, are covalently attached to an agent that provides additional functionality or enhances efficacy thereof. Such agent(s) includes, for example, a tag, label, targeting moiety or ligand, a cell binding motif or therapeutic agent, an antibacterial, an antibody, and an antibiotic.

Using turbidity reduction of stationary phase *S. aureus* as a measure of lytic activity, optimal conditions for PlyGRCS were determined, finding that it is active in the physiological range. Compared to other staphylococcal endolysins, PlyGRCS is relatively active as only 25 µg/mL produced a 70% decrease in optical density in just 15 minutes. In addition, its host range was characterized via plate lysis assays; PlyGRCS maintained lytic activity against all strains of *S. aureus* tested as well as other staphylococcal species.

Further, crystal violet staining of PlyGRCS treated biofilms demonstrated that this enzyme is suitable for use on medical devices. In some embodiments, the disclosed endolysin polypeptides and/or compositions including the endolysin polypeptide(s) of the present invention are coupled to a surface of a substrate. For example, in some implementations, a medical device (e.g., a grasper, a clamp, a retractor, a dilator, a suction, a sealing device, a scope, a probe, etc.) includes an outer surface coupled to or coated with the endolysin polypeptide(s) or composition comprising the endolysin polypeptide(s) of the present invention. In some implementations, the medical device coupled to or coated with the disclosed endolysin polypeptide(s) or composition(s) is an implantable medical device (e.g., a drainage tube, a feeding tube, a shunt, a prosthesis, a guidance tube, a catheter, a valve, a pacemaker, a graft, a tissue scaffold, a stent, etc.).

The present invention provide for methods of treating a bacterial infection in a patient comprising administering to the patient a therapeutically effective amount of an isolated endolysin polypeptide of the present invention, and in particular a polypeptide(s) comprising the amino acid sequence of SEQ ID NOs: 5, 6 and/or 7, or variants thereof such as a polypeptide(s) having at least 80% identity thereto and exhibiting comparable functionality and efficacy against bacteria associated with or causing said infection. The term "treat" or "treating" a disease, including an infectious disease or infection, refers to killing or reducing the growth of the bacteria causing such disease or infection, and/or reducing, ameliorating or eliminating symptoms associated with such disease or infection.

A "therapeutically effective amount" refers to the amount of polypeptide(s) sufficient to elicit a desired biological response in a subject, and in particular an amount sufficient to kill, reduce or stabilize a bacterial population causing such disease or infection and/or sufficient to reduce symptoms associated with such disease or infection. Preferably, a therapeutically effective amount of the polypeptide(s) of the present invention is effective in reducing growth of the bacterial population by at least about 50%, more preferably by at least about 75%, most preferably by about 90% or more.

The present invention is also directed to expression vectors prepared from the disclosed DNA sequences for expression in host systems, and encoding one or more of the endolysin polypeptide chains of the present invention. Such expression vectors may be used for recombinant production of the endolysin polypeptides of the invention. An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40 bacterial plasmids, phage DNA, baculovirus, yeast plasmids, vectors derived from combinations of plasmids and phage DNA, and viral nucleic acid (RNA or DNA) vectors.

In one embodiment, the vector is suitable for expression of an endolysin polypeptide of the present invention in a bacterial cell. Examples of such vectors include expression vectors such as BlueScript (Stratagene), pIN vectors (Van Heeke & Schuster, J. Biol. Chem. 264, 5503-5509 (1989), pET vectors (Novagen, Madison, Wis.), and the like. An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (F. Ausubel et al., ed. Current Protocols in Molecular Biology, Greene Publishing and Wiley Inter-Science New York (1987); Grant et al., Methods in Enzymol 153, 516-544 (1987); Mattanovich, D. et al. Methods Mol. Biol. 824, 329-358 (2012); Celik, E. et al. Biotechnol. Adv. 30(5), 1108-1118 (2012); and Holliger, P. Methods Mol. Biol. 178, 349-357 (2002)).

In an expression vector of the present invention, nucleic acids encoding the disclosed polypeptides may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. Any host cell capable of overexpressing heterologous DNAs can be used for the purpose of isolating the genes encoding the polypeptide or protein of interest, including for example, eukaryotic and prokaryotic hosts (e.g., strains of *E. coli, Pseudomonas, Bacillus, Streptomyces*, yeasts, etc.). As understood by those skilled in the art, not all vectors expression control sequences and hosts will function equally well to express the DNA sequences of the present invention. However, those skilled in the art will be able to readily select the proper vectors, expression control sequences, and hosts to achieve the desired expression.

The present invention provides for nucleic acids capable of encoding the disclosed endolysin polypeptide(s). "Primer" as used herein refers to an oligonucleotide that is capable of acting as a point of initiation of synthesis when placed under suitable conditions in which synthesis of a primer extension product is induced. The primer may be either single-stranded or double-stranded and sufficiently long to prime the synthesis of the desired extension product in the presence of an inducing agent. Exemplary primers are provided in Table 2 below.

The present invention also relates to pharmaceutical compositions containing therapeutically effective amounts of PlyGRCS endolysin(s) and/or variants and active fragments thereof. The pharmaceutical compositions may be formulated with pharmaceutically acceptable carriers or diluents as well as any other known adjuvants and excipients in accordance with conventional techniques such as those disclosed in Remington: *The Science and Practice of Pharmacy*, 21th Edition, Gennaro, Ed., Mack Publishing Co., Easton, Pa., 2005.

The pharmaceutically acceptable carriers or diluents, as well as any other known adjuvants and excipients, should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may thus include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in the composition. The diluent is selected to not affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredient(s) in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions of the present invention may be administered by any suitable route and mode, including: parenteral, topical, oral or intranasal means for prophylactic and/or therapeutic treatment. In one embodiment, a pharmaceutical composition of the present invention is administered orally. In another embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. Additional suitable routes of administering a compound of the present invention in vivo and in vitro are well known in the art and may be selected by those of ordinary skill in the art.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts and may alternatively or additionally be included.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Pharmaceutical compositions of the present invention may also comprise isotonicity agents, such as sugars, polyalcohols, such as mannitol, sorbitol, glycerol or sodium chloride in the compositions.

Pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition.

The pharmaceutical compositions of the present invention may include a secondary therapeutic agent in addition to therapeutically effective amounts of the endolysin polypeptides disclosed herein, such as for example an additional antimicrobial, antibiotic, and/or lytic enzyme.

The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., *Sustained and Controlled Release Drug Delivery Systems*, J. R. Robinson, ed., Marcel Dekker, Inc., New York, 1978.

In one embodiment, the compounds of the present invention may be formulated to ensure proper distribution and efficacy in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound(s), use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In some cases, it will be preferable to include isotonic agents, for example, sugars, polyalcohols such as glycerol, mannitol, sorbitol, or sodium chloride in the composition. Prolonged absorption of the compositions may be brought about by including in the composition an agent that delays absorption, for example, monostearate salts and gelatin. Sterile solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses are adjusted to provide the optimum desired response (e.g., a therapeutic response). For example, a single bolus may be administered, several divided doses may be administered over time, or the dose may be proportionally reduced or increased as indicated by the exigencies of the therapeutic situation. Pharmaceutical compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and dependent on (a) the characteristics of the active compound and the particular therapeutic effect to be achieved, and (b) any limitations in the art of compounding such an active compound for the treatment of sensitivity in individuals.

A physician having ordinary skill in the art may readily determine and prescribe the therapeutically effective amount of the pharmaceutical composition required for a particular patient. Such amount may vary according to factors such as the disease state, age, sex, and weight of the patient. In addition, the therapeutically effective amount is one in which any toxic or detrimental effects of the pharmaceutical composition are outweighed by the therapeutically beneficial effects. The physician may start doses of the endolysin polypeptide(s) in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce the desired therapeutic effect (e.g., killing gram-positive bacteria, and in particular *Staphylococcus* species, e.g., *S. aureus* and *S. epidermidis*, and including methicillin- and vancomycin-resistant strains (e.g., MRSA, VISA, MRSE), and/or for treating or preventing infection, and/or for ameliorating or alleviating symptoms associated with such bacteria in a subject). Such an effective dose will generally depend upon the factors described above. While it is possible for a compound of the present invention to be administered alone, it is preferable to administer the compound as a pharmaceutical composition as described above.

Pharmaceutical compositions in accordance with the present invention may be administered via spray, inhaler, topical, etc. Pharmaceutical compositions and polypeptides in accordance with disclosed embodiments may be administered via lozenges, chewing gums, tablets, powders, sprays, liquids, ointments, etc. Formulations including endolysin polypeptides of the present invention may include additives, stabilizers, buffers, etc. as described above.

While some embodiments are described with respect to use in humans, the endolysin polypeptides, compositions and methods of the present invention are also suitable for veterinary (non-human) applications. For example, *S. aureus* is one of the most common causes of bovine mastitis in milking cows and prevention and control of such infection is difficult. Once established, *S. aureus* infections do not respond well to conventional antibiotic therapy, and infected cows or other livestock must often be segregated or culled from the herd. The spread of such infection within a group of livestock may occur through, inter alia, human contact (e.g., milkers' hands), equipment for maintaining and processing the animals, and flies. Thus, the polypeptide(s) of the present invention may be utilized for treating bacterial infection or contamination in livestock or other animals (e.g., by administering the polypeptide(s) of the present invention to such livestock or animal orally, nasally, parenternally, onto the skin or coat, via intramammary infusion, teat dip, etc. as described herein).

The endolysin polypeptides of the present invention, and compositions comprising such polypeptides, are also suitable for use as a sanitizing agent or disinfectant of a target surface or area. Thus, the present invention provides for methods and compositions for treating or preventing bacterial contamination of dental and medical devices, surfaces in hospitals and dental and medical facilities, food processing equipment, surfaces in food processing facilities, equipment and surfaces in schools, and other equipment or surfaces on which sanitization is desired.

In addition, the compositions of the present invention may be used in combination with other disinfecting ingredients, cleaners, and agents (e.g., such as detergents, solvents, antibiotics, antimicrobials, etc.). In some implementations, endolysin polypeptide(s) and compositions of the present invention are applied to target surfaces or areas as a liquid or spray formulation (e.g., aerosolized or mist formulation). Disclosed compositions may be applied, e.g., with a dry mist fogger or other such application, for disinfecting surfaces within a target area or volume (e.g., a milking parlor, school gymnasium or auditorium, surgical suite, medical equipment, etc.).

Additional characteristics and features of the present invention will be further understood through reference to the following examples and discussion, which are provided by way of further illustration and are not intended to be limiting of the present invention.

Materials and Methods
Bacterial Strains.
Tested bacterial species, strains, and associated antimicrobial resistance phenotypes are shown in Table 1 below.

TABLE 1

PlyGRCS Host Range

| Bacterial species, strains tested[1] | Resistance[2] | PlyGRCS[3] | CHAP$_{GRCS}$ |
|---|---|---|---|
| *Staphylococcus aureus*, NRS-385 | MRSA | + | − |
| *Staphylococcus aureus*, NRS-382 | MRSA | + | − |
| *Staphylococcus aureus*, NRS-384 | MRSA | + | + |
| *Staphylococcus aureus*, NRS-71 | MRSA | ++ | + |
| *Staphylococcus aureus*, NRS-14 | VISA | ++ | − |
| *Staphylococcus epidermidis*, NRS-101 | MRSE | ++ | + |
| *Streptococcus suis*, 730082 | | − | − |
| *Streptococcus pyogenes*, D471 | | − | − |
| *Streptococcus pneumoniae*, ATCC BAA-334 | | − | − |
| *Streptococcus uberis*, ATCC 700407 | | − | − |
| *Streptococcus equi*, ATCC 9528 | | − | − |
| *Bacillus pumulis*, BJ0055 | | − | − |
| *Enterococcus faecalis*, EF24 | | − | − |

[1]See below for source of strains.
[2]MRSA: methicillin-resistant *S. aureus*; VISA: vancomycin intermediate-resistant *S. aureus*; MRSE: methicillin-resistant *S. epidermidis*.
[3]Activity of 6 µg PlyGRCS or CHAP$_{GRCS}$ was evaluated via plate lysis assays. The strength of lytic zones was defined qualitatively: strong lytic zone = ++, weak lytic zone = +, no lytic zone = −.

All staphylococci containing the NRS strain designations were provided by the Network on Antimicrobial Resistance in *S. aureus* (NARSA), which is distributed by BEI Resources depository (Manassas, Va.) under the direction of the National Institute of Allergy and Infectious Diseases and the National Institutes of Health. A *Streptococcus suis* clinical isolate was obtained from Dr. Randy Shirbroun at Newport Laboratories (Worthington, Minn.). *Streptococcus pyogenes* and *Enterococcus facealis* were obtained from Drs. Vincent Fischetti and Alexander Tomasz, respectively, at The Rockefeller University, USA). A *Bacillus pumulis* clinical isolate was obtained from Dr. John Mayo at Louisiana State University, USA. The remaining strains, *Streptococcus pneumonia, Streptococcus uberis,* and *Streptococcus equi*, were obtained from the American Type Culture Collection (ATCC).

All strains were stored at −80° C. and routinely grown at 37° C. Streptococcal strains were grown in Todd-Hewitt broth, supplemented with 1% yeast extract (THY) (Alpha Bioscience), or on THY plates; staphylococcal strains, *B. pumulis*, and *E. facealis*, were grown in trypticase soy broth (TSB) (Becton-Dickinson), or on TSB plates; *Escherichia coli* was cultivated in Luria Broth (LB) (Alpha Bioscience), or on LB plates. Chemicals were purchased from Sigma and were of the highest purity available.

Cloning, Domain Constructs, and Site-Directed Mutagenesis.

The phage GRCS genome has recently been elucidated (GenBank Accession KJ210330) (Swift S M & Nelson D C (2014) *Complete genome sequence of Staphylococcus aureus phage GRCS*. Genome Announc 2(2)). Bioinformatic analysis using BLAST and PFAM programs [National Center for Biotechnology Information (NCBI)] predicted a putative endolysin for ORF15 (AHJ10590), referred to as PlyGRCS. As noted above, PlyGRCS contains an N-terminal cysteine, histidine-dependent amidohydrolase/peptidase (CHAP) catalytic domain and a C-terminal bacterial src-homology 3 (SH3_5) binding domain.

Individual domain clones for CHAP (i.e. $CHAP_{GRCS}$) and SH3_5 (i.e. $SH3\_5_{GRCS}$) were amplified using the primer pairs shown in Table 2.

TABLE 2

Primers

| Primer | Sequence |
|---|---|
| CHAP-F | 5'-GGGGAATTCATTATGAAATCACAACAACAAG CAAAAGAATGGATATA-3' (SEQ ID NO: 8) |
| CHAP-R | 5'-AAATCTAGATTAATGATGATGATGATGA CTAGCAGAAAATTTAG-3' (SEQ ID NO: 9) |
| SH3_5F | 5'-GGGGAATTCATTATGAATACATTTGGAAATT GGAAACAAAACCAATAC-3' (SEQ ID NO: 10) |
| SH3_5R | 5'-AAATCTAGATTAATGATGATGATGATGATGT GAGAACACCCCCCAAG-3' (SEQ ID NO: 11) |
| C29S | 5'-[Phos]-GCATATGGTTTTCAAAGCATGGACTTAGCTGTT-3' (SEQ ID NO: 12) |
| H92A | 5'-[Phos]-AATTCTCAATATGGTGCGATTCAATGTGTAATA-3' (SEQ ID NO: 13) |

For the full-length PlyGRCS, the CHAP-F and SH3_5R primers were utilized. All reverse primers incorporated a 6× His purification tag. Specific point mutations to putative active-site residues (C29S and H92A) were made with phosphorylated primers (Table 2) using the Change-IT Multiple Mutation Site Directed Mutagenesis Kit (Affymetrix USB) according to the manufacturer's instructions. All PCR products were cloned into pBAD24, transformed into *E. coli* BL21 (DE3) cells and consequently sequenced (Macrogen, Rockville, Md.). The ApE program (University of Utah) was utilized for DNA sequence analysis and manipulations.

Expression and Purification.

*E. coli* were grown at 37° C. in baffled flasks to an $OD_{600}=1$ in LB supplemented with 100 μg/ml ampicillin. Expression was induced with 0.25% arabinose overnight at 18° C. Crude protein extracts were purified by a Bio-Scale Mini Profinity IMAC Cartridge (Bio-Rad) and eluted in 10 ml fractions of 20 mM, 50 mM, 100 mM, 250 mM, and 500 mM imidazole, followed by SDS-PAGE analysis. Fractions containing proteins of the correct predicted molecular weight were pooled and dialyzed against PBS pH 7.4 with 300 mM NaCl.

Quantification of Lytic Activity.

Lytic activity was based on turbidity reduction assay (Nelson D C et al. (2012) Endolysins as antimicrobials. Adv Virus Res 83:299-365). Briefly, bacterial cells were centrifuged (4,000 RPM, 5 minutes, 4° C.), re-suspended in buffer and mixed 1:1 (v/v) with endolysin to a final $OD_{600}=1$. $OD_{600}$ readings were taken every 15 seconds for 20 minutes at 37° C. Endolysin activity was equated to the $V_{max}$ dictated by the linear portion of the resulting killing curve. Each experiment was performed in triplicate.

Characterization of PlyGRCS.

To determine dose response, PlyGRCS was serially diluted and each dosage (100 μl) was added in triplicate to a 96-well polystyrene microtiter plate (Nest Biotech Co, Ltd) just before addition of bacterial cells (100 μl) according to the turbidity reduction assay described above. For optimum pH determination, bacterial cells were suspended in 40 mM boric acid/phosphoric acid (BP) buffer, pH 3-11, and were challenged against PlyGRCS. The influence of NaCl on PlyGRCS activity was tested in BP buffer at the experimentally determined pH optimum using the same assay. The effect of divalent cations was determined using the turbidity reduction assay with several modifications. First, PlyGRCS was incubated at room temperature in PBS or PBS supplemented with 5 mM EDTA for 10 minutes. Second, the EDTA-treated samples received either no further treatment, or were supplemented with 6 mM $CaCl_2$ or 6 mM $MgCl_2$. Finally, the lytic active of the samples was then immediately assayed and compared to PlyGRCS in PBS prior to EDTA inactivation. Kinetic stability was evaluated (Son B et al. (2012) *Characterization of LysB4, an endolysin from the Bacillus cereus-infecting bacteriophage B4*. BMC Microbiol 12:33) with minor modifications. Lytic assays were performed in optimal conditions after PlyGRCS was incubated at indicated temperatures for 30 minutes and subsequently recovered on ice for 5 minutes.

Cell Wall Binding.

An overnight culture of *S. aureus* NRS-14 was concentrated 5× in BP buffer and was incubated at room temperature with 10 μg $SH3\_5_{GRCS}$ containing the 6× His tag for 10 minutes. A control without $SH3\_5_{GRCS}$ was also utilized. The samples were washed with PBS and incubated for 10 minutes at room temperature with 1 μl mouse anti-His antibody (Gen Script). After washing with PBS, AlexaFluor-488 conjugated goat anti-mouse IgG (H+L) antibody (1 μl) (Invitrogen) was incubated with samples for an additional 10 minutes. Samples were washed again with PBS before being visualized via fluorescence and bright field microscopy. An Eclipse 80i epifluorescent microscope workstation (Nikon)

with X-Cite 120 illuminator (EXFO) and Retiga 2000R CCD camera was used. NIS-Elements software (Nikon) was used for image analysis.

Spectrum of Lytic Activity.

The PlyGRCS spectrum of lytic activity was performed (Schmelcher M et al. (2012) *Chimeric phage lysins act synergistically with lysostaphin to kill mastitis-causing Staphylococcus aureus in murine mammary glands*. Appl Environ Microbiol 78(7):2297-305) with minor modifications. Bacterial cells were diluted in sterile PBS to an $OD_{600}=1$, and 100 µl was spread on each plate. 10 µl spots (600 µg/ml) of PlyGRCS or $CHAP_{GRCS}$ were applied. Plates were incubated overnight at 37° C. Strength of lytic zones was defined qualitatively.

Biofilm Assay.

An overnight culture of *S. aureus* NRS-14 (1 ml per well) was placed into 24-well CELLBIND plates (Corning) containing 500 µl of TSB per well. After an additional 24 hour incubation at 37° C., media was aspirated and samples were washed with PBS to remove unattached cells. Two-fold serial dilutions of PlyGRCS in triplicate were added in 1 ml BP buffer pH 7 and incubated at 37° C. for one hour. Liquid was aspirated and samples were washed with distilled water before drying. Biofilms were stained with 0.01% crystal violet for 10 min at room temperature. After removing the excess crystal violet, samples were washed with PBS and dried before the addition of 1 ml 10% SDS to extract the crystal violet from the biomass for quantification at $OD_{595}$.

Bactericidal Analysis.

Sterile-filtered PlyGRCS was 2-fold serially diluted in PBS supplemented with 1 mM $CaCl_2$ and an equal volume of either various concentrations of enzyme or buffer only was added to $10^5$ *S. aureus* NRS-14 in a microtiter plate. Samples were incubated at 37° C. for 1 hour, then serially diluted, plated on TSB agar, and incubated overnight at 37° C. to obtain CFU counts. The MBC (minimum bactericidal concentration) was determined as the minimum concentration of enzyme that killed ≥99.9% of bacteria.

Circular Dichroism (CD) Spectropolarimetry.

CD experiments for wild-type (WT) and active-site mutants were performed on a Chirascan CD spectrometer (Applied Photophysics) equipped with a thermoelectrically controlled cell holder. CD spectra were obtained in the far-UV range (190-260 nm) in a 1 mm path length quartz cuvette at 1 nm steps with 5 second signal averaging per data point. Spectra were collected in triplicate, followed by averaging, baseline subtraction, smoothing and conversion to mean residue ellipticity (MRE) by the Pro-Data software (Applied Photophysics). Secondary structure prediction was performed using the Provencher and Glockner method (Provencher S W & Glockner J (1981) *Estimation of globular protein secondary structure from circular dichroism*. Biochemistry 20(1):33-7) provided by DICHROWEB (Whitmore L & Wallace B A (2004) *DICHROWEB, an online server for protein secondary structure analyses from circular dichroism spectroscopic data*. Nucleic Acids Res 32:W668-73).

Melting experiments were performed by heating PlyGRCS at a 0.1 mg/ml concentration in 20 mM sodium phosphate buffer pH 7 from 20° C. to 95° C. using a 1° C./min heating rate. MRE was monitored at 218 nm in a 1 mm path length quartz cuvette at 0.5° C. steps with 5 second signal averaging per data point. The melting data was smoothed, normalized and fit with a Boltzmann sigmoidal curve. The first derivative of the melting curve was then taken to determine the temperature ($T_m$) at which the folded and unfolded protein species in solution were at equilibrium (Fallas J A & Hartgerink J D (2012) *Computational design of self-assembling register-specific collagen heterotrimers*. Nat Commun 3:1087).

Biochemical Assays.

For analysis of reducing sugars released from the peptidoglycan, the dinitrosalicylic acid (DNSA) assay was used (Danner M et al. (1993) *Folding and assembly of phage P22 tailspike endorhamnosidase lacking the N-terminal, head-binding domain*. Eur J Biochem 215(3):653-61). *S. aureus* NRS-14 peptidoglycan was purified (Pritchard D G et al. (2004) *The bifunctional peptidoglycan lysin of Streptococcus agalactiae bacteriophage B30*. Microbiology 150(Pt 7):2079-87; Schmelcher M et al. (2012) *Listeria bacteriophage peptidoglycan hydrolases feature high thermoresistance and reveal increased activity after divalent metal cation substitution*. Appl Microbiol Biotechnol 93(2):633-43), and treated for one hour at 37° C. with 50 µg/ml of PlyGRCS in optimal conditions. Samples were centrifuged and the supernatant was added to an equal volume of 87.7 mM DNSA (20 g/L in 0.7 M NaOH). After boiling for 5 mM, samples were allowed to cool and the absorbance was read at $OD_{535}$. Known concentrations of glucose were used to create a standard curve. To determine an increase in free amine groups, the trinitrophenylation reaction was used, originally described by Satake et al. and modified by Mokrasch (Satake M et al. (1960) *Incorporation of leucine into microsomalprotein by a cell-free system of guinea-pig brain*. Biochim Biophys Acta 41:366-7; Mokrasch L (1967) *Use of 2,4,6-trinitrobenzenesulfonic acid for the coestimation of amines, amino acids, and proteins in mixtures*. Anal Biochem 18:64-71). Purified peptidoglycan ($OD_{600}=1$) was treated with PlyGRCS (50 µg/ml) for one hour at 37° C. Samples were pelleted and the supernatant was filtered through a 0.22 µM filter. The sterile filtrate was added to sodium tetraborate and trinitrobenzenesulfonic acid and incubated for 30 minutes at room temperature. Samples were read at $OD_{420}$. Lysine was used as a standard.

Cleavage Analysis by Mass Spectrometry.

For determination of cut sites within the staphylococcal peptidoglycan, purified cell walls were digested with PlyGRCS and the resulting fragments were analyzed via mass spectrometry (Becker S C et al. (2009) *LysK CHAP endopeptidase domain is required for lysis of live staphylococcal cells*. FEMS Microbiol Lett 294(1):52-60; Pritchard D G et al. (2004) *The bifunctional peptidoglycan lysin of Streptococcus agalactiae bacteriophage B30*. Microbiology 150(Pt 7):2079-87). Briefly, SA113 ΔtagO cell walls (Atilano M L et al. (2010) *Teichoic acids are temporal and spatial regulators of peptidoglycan cross-linking in Staphylococcus aureus*. Proc Natl Acad Sci USA 107(44):18991-6; Weidenmaier C et al. (2004) *Role of teichoic acids in Staphylococcus aureus nasal colonization, a major risk factor in nosocomial infections*. Nat Med 10(3):243-5) were digested in 25 mM Tris, 200 mM NaCl, pH 7.4 at 37° C. for 18 hours with 50 µg/ml of PlyGRCS, filtered through 5000-MW cutoff Vivaspin 500 units (Sartorius North America Inc., Bohemia, N.Y.), and desalted using C18 Zip Tips (Millipore, Zug, Switzerland). Controls included peptidoglycan digested with the amidase domain of 2638A, a known N-acetylmuramoyl-L-alanine amidase, or undigested peptidoglycan. To further define the PlyGRCS cut site, double digests with PlyGRCS and a truncation construct containing only the CHAP domain of LysK (CHAP-K), a D-alany-glycyl endopeptidase were performed. The samples were eluted from the Zip Tips with 50:50:0.01 (v/v/v)

CH$_3$OH:H$_2$O:HCOH (pH~2), and NanoESI-MS analysis was performed on a Q-TOF Ultima API mass spectrometer (Micromass, UK).

Results

Expression of PlyGRCS and Domain Constructs.

The phage GRCS genome was recently sequenced (KJ210330) (Swift S M & Nelson D C (2014) *Complete genome sequence of Staphylococcus aureus phage GRCS*. Genome Announc 2(2)). Bioinformatic analysis predicted an endolysin for ORF15 (AHJ10590), referred to as PlyGRCS. This enzyme contains a putative N-terminal CHAP domain, which is shown to encompass bacteriolytic activity in other characterized endolysins, and a C-terminal bacterial src-homology 3 (SH3_5) domain that functions as a CBD in many staphylococcal and streptococcal endolysins (Nelson D C et al. (2012) *Endolysins as antimicrobials*. Adv Virus Res 83:299-365).

The closest homologs to PlyGRCS are a hypothetical protein from *S. aureus* 2011-60-1490-31 (EZV76040.1, 98% identity), an amidase from *Staphylococcus* phage 44AHJD (NP_817310.1, 96% identity), ORF009 of *Staphylococcus* phage 66 (YP_239469.1, 97% identity), the SAL-2 amidase from *Staphylococcus* phage SAP-2 (YP_001491539.1, 96% identity), and an unnamed protein product of *Staphylococcus* phage S24-1 (YP_004957430.1, 92% identity). To study the full-length enzyme and elucidate the contributions of each domain, the full length PlyGRCS was cloned, as well as its isolated CHAP domain (CHAP$_{GRCS}$, amino acids 1-140) and SH3_5 domain (SH3_5$_{GRCS}$, amino acids 150-250) into expression vectors. All three constructs were expressed as soluble proteins and purified to homogeneity by nickel affinity chromatography via the C-terminal 6× His tags on each protein.

Characterization of PlyGRCS.

Figure 2:
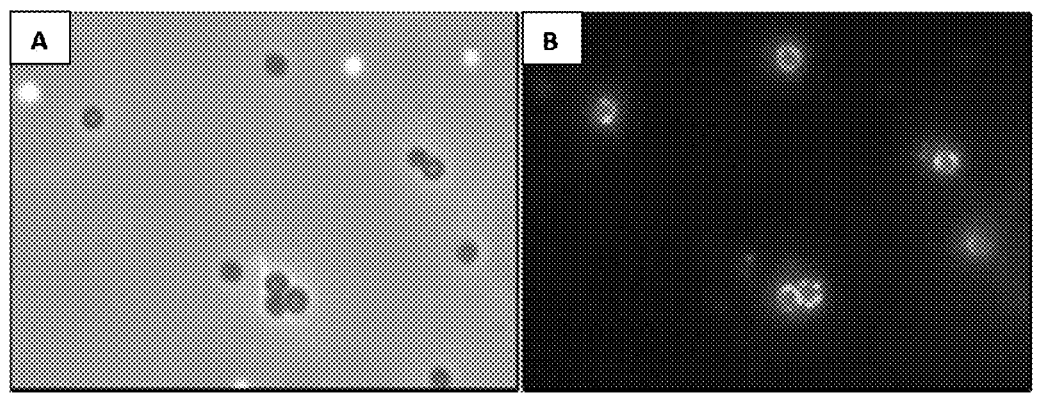
FIG. 2 are brightfield (FIG. 2, Plate A) and fluorescent (FIG. 2, Plate B) images showing $SH3\_5_{GRCS}$ directly interacting with *S. aureus* NRS-14. PlyGRCS contains a C-terminal cell wall binding domain. Cell wall binding was detected via Mouse Anti-His and Goat Anti-Mouse IgG AlexaFluor 488.

PlyGRCS displayed a dose response curve from 28 to 1.75 µg/ml when tested in a turbidity reduction assay using stationary phase *S. aureus* NRS-14 cells (FIG. 1, Plate A). The highest dose corresponded to a 70% decrease in optical density in just 15 minutes (50% decrease in <10 minutes). When tested at equimolar concentrations, CHAP$_{GRCS}$ displayed ~8-10% of full-length PlyGRCS activity. In contrast, SH3_5$_{GRCS}$ displayed little to no lytic activity; however, this domain alone possessed the ability to specifically bind staphylococci as detected by antibody recognition of the 6× His purification tag on the staphylococcal surface (FIG. 2). Control experiments without SH3_5$_{GRCS}$ did demonstrate binding of the antibody. Therefore, while the CHAP domain is independently capable of lysing *S. aureus*, for some applications, enhanced antimicrobial efficacy of the endolysin is provided by the simultaneous presence of both the CHAP and SH3_5$_{GRCS}$ domains.

Lytic activity of PlyGRCS was then tested in BP buffer with a pH range from 3.0 to 11.0 to determine optimum conditions. Optimal pH was determined to be 7.0, with an active range between 6.0 and 8.0 (FIG. 1, Plate B). PlyGRCS activity was markedly reduced at pH extremes. Based on the above observations, subsequent turbidity reduction and antimicrobial assays were performed in BP buffer pH 7.0. Because the activity of many endolysins, including various staphylococcal endolysins (Becker S C et al. (2008) *The phage K lytic enzyme LysK and lysostaphin act synergistically to kill MRSA*. FEMS Microbiol Lett 287(2):185-91; Garcia P et al. (2010) *Synergy between the phage endolysin LysH5 and nisin to kill Staphylococcus aureus in pasteurized milk*. Int J Food Microbiol 141(3):151-5), is enhanced by the addition of NaCl, we investigated the activity of PlyGRCS in the presence of NaCl ranging from 0 to 500 mM. Surprisingly, NaCl had little effect (±10%) on PlyGRCS activity up to 125 mM and only slightly inhibited activity at higher concentrations (~35% decrease at 500 mM) (FIG. 1, Plate C).

Several other CHAP domain-containing staphylococcal endolysins (Donovan D M et al. (2006) *Lysis of staphylococcal mastitis pathogens by bacteriophage phi11endolysin*. FEMS Microbiol Lett 265(1):133-9; Fenton M et al. (2011) *Characterization of the staphylococcal bacteriophage lysin CHAP(K)*. J Appl Microbiol 111(4):1025-35), as well as streptococcal endolysins (Celia L K et al. (2008) *Characterization of a bacteriophage lysin (Ply700) from Streptococcus uberis*. Vet Microbiol 130(1-2):107-17; Pritchard D G et al. (2004) *The bifunctional peptidoglycan lysin of Streptococcus agalactiae bacteriophage B30*. Microbiology 150(Pt 7):2079-87) have been shown to require calcium for activity. Furthermore, the structure of the staphylococcal LysGH15 CHAP domain shows calcium in an EF-hand-like structure (Gu J et al. (2014) *Structural and biochemical characterization reveals LysGH15 as an unprecedented "EF-Hand-like" calcium-binding phage lysin*. PLoS pathogens 10(5):e1004109). The CHAP domain of PlyGRCS shares identity in three aspartic acid residues known to complex this cation in LysGH15 and other calcium-binding proteins, although it only shows 42% in overall identity with the LysGH15 CHAP domain.

With this in mind, the activity of PlyGRCS was analyzed in either the presence or absence of calcium. PlyGRCS was first incubated with EDTA to remove all divalent cations from solution. EDTA-treated PlyGRCS was devoid of lytic activity (FIG. 1, Plate D). Next, EDTA-treated PlyGRCS was incubated with excess CaCl$_2$. Calcium-treated PlyGRCS displayed nearly twice the lytic activity when compared to PlyGRCS prior to EDTA treatment. To determine whether divalent metal dependence of PlyGRCS is specific to calcium, the activity of the EDTA-treated endolysin was measured after the addition of an alternative divalent metal, magnesium. The activity of magnesium-treated PlyGRCS mimicked that of the EDTA-treated sample, indicating that the divalent metal dependence of PlyGRCS is calcium-specific.

Figure 3:
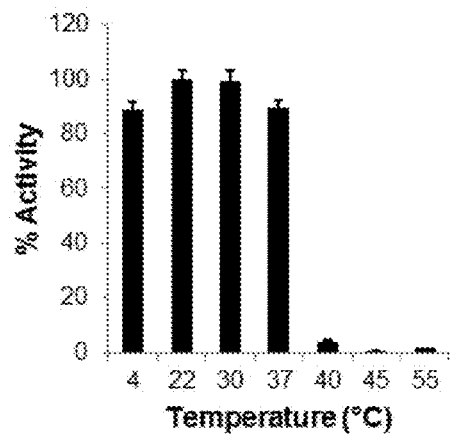
FIG. 3 illustrates PlyGRCS temperature stability. Stationary phase *S. aureus* NRS-14 treated with 25 μg/ml of PlyGRCS after being held at indicated temperatures for 30 min and recovered on ice for 5 min is shown in FIG. 3, Plate A. The thermal stability of full length PlyGRCS (FIG. 3, Plate B) as well as $CHAP_{GRCS}$ (FIG. 3, Plate C) and $SH3\_5_{GRCS}$ (FIG. 3, Plate D) was determined by means of circular dichroism (CD) melting experiments. Samples were heated from 20° C. to 95° C. at 1° C./min in 20 mM sodium phosphate buffer pH 7 using a protein concentration of 0.1 mg/ml.
Figure 3:
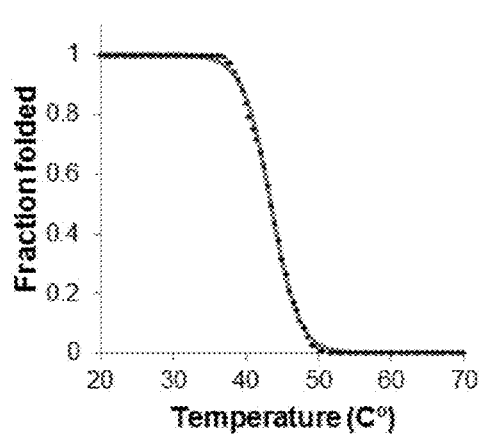
Figure 3:
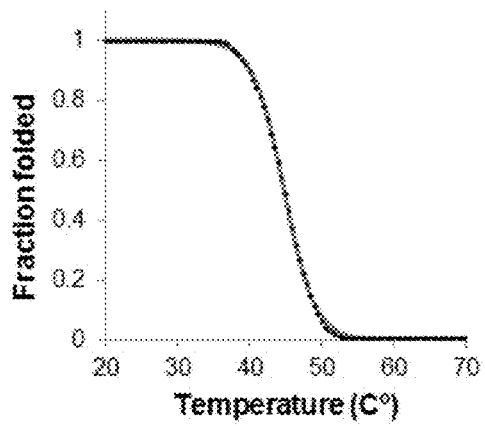
Figure 3:
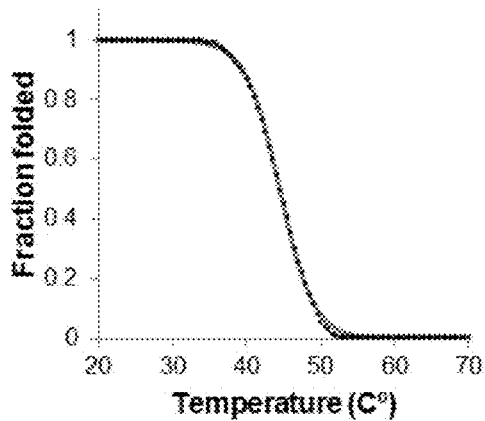

Finally, the kinetic and thermodynamic stability of PlyGRCS was investigated. PlyGRCS displayed >90% residual lytic activity after incubating at temperatures ranging from 4° C. to 37° C. for a total of 30 minutes. At temperatures of ≥40° C., lytic activity was not observed (FIG. 3, Plate A). Melting experiments performed on a CD spectrophotometer show cooperative unfolding of PlyGRCS with a T$_m$ of 43.5° C. (FIG. 3, Plate B), which further confirms the lack of activity at ≥40° C. observed during the kinetic stability experiment. CHAP$_{GRCS}$ (FIG. 3, Plate C) and SH3_5$_{GRCS}$ (FIG. 3, Plate D) had similar T$_m$ values of 44.8° C. and 44.5° C., respectively. The observed PlyGRCS stability profile is consistent with that of other phage lysins. For example, the *S. aureus* endolysin LysK is kinetically inactivated at 42.0° C. and the *Streptococcus pneumoniae* endolysin Cpl-1 displays at T$_m$ of 43.5° C. (Filatova L Y et al. (2010) *LysK, the enzyme lysing Staphylococcus aureus cells: specific kinetic features and approaches towards stabilization*. Biochimie 92(5):507-13; Sanz J M et al. (1993) *Thermal stability and cooperative domains of CPL1 lysozyme and its NH2-and COOH-terminal modules. Dependence on choline binding*. J Biol Chem 268(9):6125-30).

PlyGRCS Spectrum of Lytic Activity.

In order to determine the spectrum of lytic activity of PlyGRCS, activity was tested against 13 different bacterial strains including methicillin-resistant and vancomycin-intermediate resistant *S. aureus*, methicillin-resistant *S. epidermidis*, and several other representative Gram-positive pathogens (see Table 1). At 6 µg, lytic activity was seen against all staphylococcal strains, with PlyGRCS exhibiting the greatest strength against *S. aureus* strains NRS-71 and NRS-14 and *S. epidermidis* NRS-101. CHAP$_{GRCS}$ exhibited less activity, causing relatively weak clearing zones on plates of *S. aureus* strains NRS-384 and NRS-71 and *S. epidermidis* NRS-101. Little to no lytic activity was observed on other strains. Thus, PlyGRCS has an activity spectrum relatively confined to staphylococcal species, as little or no activity was observed against tested streptococci or representative bacilli and enterococci species (Table 1).

Biofilm Assay.

Figure 4:
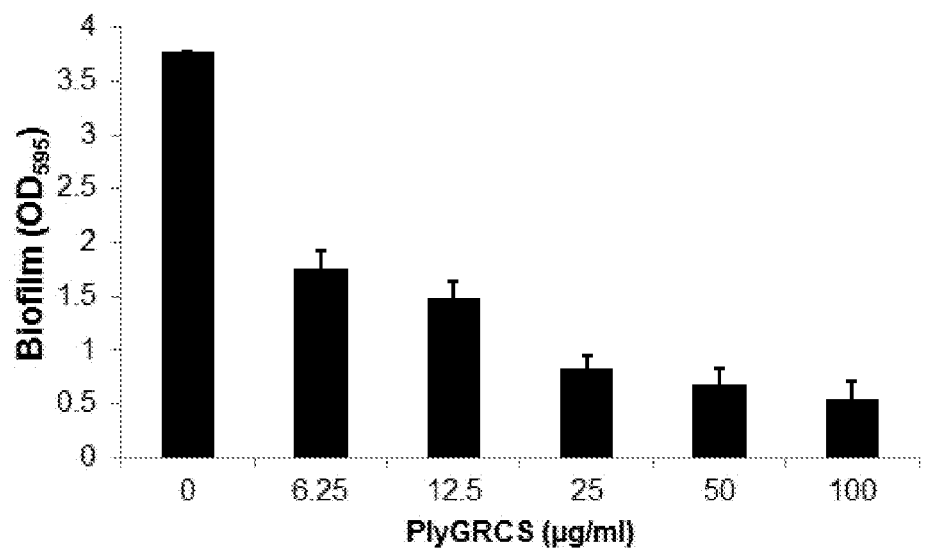
FIG. 4 illustrates antibiofilm activity of PlyGRCS. *S. aureus* NRS-14 was allowed to form static biofilms for 24 hours and treated with PlyGRCS at indicated concentrations for 1 hour. The amount of biofilm is represented by the quantification of crystal violet staining of biomass at $OD_{595}$. Error bars represent the standard deviation, and all experiments were done in triplicate.

Considering the ability of *S. aureus* to form biofilms and thus present a further barrier to traditional treatments, we investigated the anti-biofilm properties of PlyGRCS. When 1 day biofilms were treated with PlyGRCS for 1 hour, a dose response decrease in the amount of biofilm was visualized, with as little as 6.25 µg/ml affecting a ~50% decrease in biofilm biomass (FIG. 4).

Bactericidal Effects of PlyGRCS.

It has been noted that the minimal inhibitory concentration (MIC) assay may not be the most appropriate assay to measure endolysin efficacy due to the speed at which the enzyme acts (Kusuma C M et al. (2005) *Comparison of four methods for determining lysostaphin susceptibility of various strains of Staphylococcus aureus*. Antimicrobial agents and chemotherapy 49(8):3256-63). Therefore, we employed the minimum bactericidal concentration (MBC) assay, which is the lowest concentration of enzyme that kills ≥99.9% (i.e. 3 logs) of the test inoculum (Jones R et al. (1985) *Susceptibility tests: microdilution and macrodilution broth procedures*. In: Balows A, Hausler J, Shadomy H (eds) Manual of Clinical Microbiology. American Society for Microbiology, Washington, D.C., pp 972-7).

When tested against a VISA strain in stationary phase, 25 µg/ml PlyGRCS resulted in 3 log killing, 12.5 µg/ml yielded a 2.5 log decrease, and 6.25 µg/ml reduced bacterial counts by 2 logs. Of note, VISA strains possess thicker cell walls than other *S. aureus* strains. This phenotype may cause the bacteria to be more resilient to endolysin treatment, and hence require higher than normal MBC values (Howden B P et al. (2010) *Reduced vancomycin susceptibility in Staphylococcus aureus, including vancomycin-intermediate and heterogeneous vancomycin-intermediate strains: resistance mechanisms, laboratory detection, and clinical implications*. Clin Microbiol Rev 23(1):99-139; Sieradzki K et al. (2003) *Alterations of cell wall structure and metabolism accompany reduced susceptibility to vancomycin in an isogenic series of clinical isolates of Staphylococcus aureus*. J Bacteriol 185(24):7103-10). Nonetheless, the results compare favorably to other anti-staphylococcal endolysins. For example, PlySs2 represents the only other staphylococcal endolysin with reported bactericidal activity against a VISA strain, requiring 128 µg/ml to decrease the colony counts of mid-log phase cells by 2 logs (Gilmer et al. (2013) *Novel bacteriophage lysin with broad lytic activity protects against mixed infection by Streptococcus pyogenes and methicillin-resistant Staphylococcus aureus*. Antimicrob Agents Chemother 57(6):2743-50).

Confirmation of N-Terminal CHAP Catalytic Domain.

By definition, CHAP domains contain two invariant residues, a cysteine and a histidine (Bateman A & Rawlings N D (2003) *The CHAP domain: a large family of amidases including GSP amidase and peptidoglycan hydrolases*. Trends Biochem Sci 28(5):234-7; Rigden D J et al. (2003) *Amidase domains from bacterial and phage autolysins define a family of gamma-D,L-glutamate-specific amidohydrolases*. Trends Biochem Sci 28(5):230-4). The cysteine acts as a catalytic nucleophile and the histidine may function as a general base to deprotonate the thiol group of the cysteine.

Figure 5:
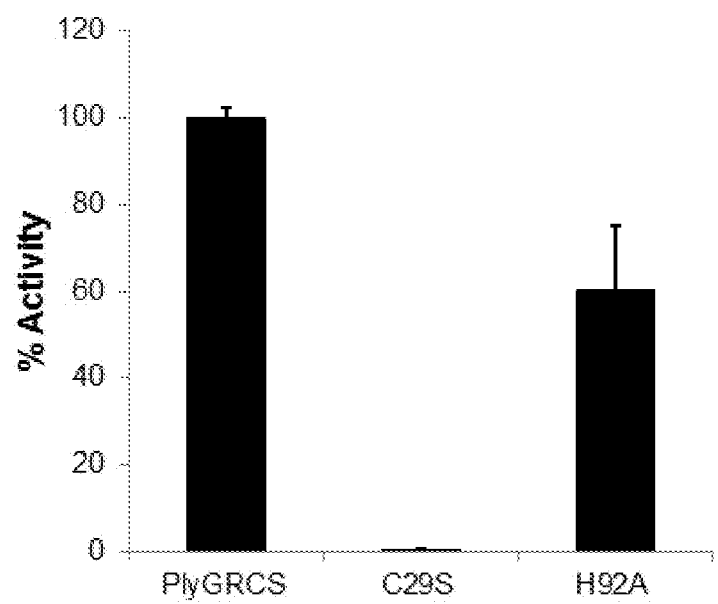
FIG. 5 illustrates stationary phase *S. aureus* NRS-14 treated with 25 μg/ml PlyGRCS, PlyGRCS-C29S, or PlyGRCS-H92A. PlyGRCS contains an N-terminal catalytic domain with an active-site cysteine and histidine. The reduction in activity of PlyGRCS-C29S and PlyGRCS-H92A indicates that these are the active-site residues. Error bars represent the standard deviation, and all experiments were done in triplicate.

To determine the contributions of these putative residues in PlyGRCS, we used site-directed mutagenesis to alter C29 and H92, the residues identified by a PFAM alignment of PlyGRCS to archetypical CHAP domains. Circular dichroism analysis demonstrated that both the C29S and H92A point mutants had similar secondary structures to WT PlyGRCS. No lytic activity was observed when the C29S mutant was used against *S. aureus* NRS-14 in a turbidity reduction assay (FIG. 5); however, H92A still exhibited lytic activity, although reduced to about 40% as compared to WT activity. Similar mutagenesis of active-site histidine residues in cysteine proteases have likewise displayed reduced but measurable activity (Ekici O D et al. (2008) *Unconventional serine proteases: variations on the catalytic Ser/His/Asp triad configuration*. Protein science: a publication of the Protein Society 17(12):2023-37; Khayat R et al. (2001) *Investigating the role of histidine* 157 *in the catalytic activity of human cytomegalovirus protease*. Biochemistry 40(21): 6344-51). Thus, other residues near the active-site residues may substitute for the histidine as an electron acceptor during the nucleophilic attack by the cysteine.

Cleavage Specificity of the CHAP Domain.

CHAP domains are associated with N-muramoyl-L-alanine amidase (amidase) or endopeptidase activity (Bateman A & Rawlings N D (2003) *The CHAP domain: a large family of amidases including GSP amidase and peptidoglycan hydrolases*. Trends Biochem Sci 28(5):234-7). Specifically, CHAP domains of staphylococcal endolysins have been characterized as amidases or D-alanyl-glycyl endopeptidases (Schmelcher M et al. (2012) *Bacteriophage endolysins as novel antimicrobials*. Future Microbiol 7(10):1147-71). To determine the specific catalytic nature of the PlyGRCS CHAP domain, two biochemical assays were employed to analyze the reducing sugar (indicative of glycosidase activity) or amine (indicative of amidase/endopeptidase activity) release upon PlyGRCS treatment. As expected, PlyGRCS did not show any glycosidase activity. However, free amines were detected when *S. aureus* cell walls were treated with PlyGRCS, demonstrating that the catalytic activity is indeed an amidase or endopeptidase.

To further elucidate which hydrolytic activity PlyGRCS possesses, enzymatically digested *S. aureus* peptidoglycan preparations were subjected to electron spray ionization-mass spectrometry (ESI-MS). Unexpectedly, the PlyGRCS digest (FIG. 6, Plate A, top spectrum) revealed a peak at m/z=702.35, which could only be produced by the presence of two enzymatic activities, an N-acetylmuramoyl-L-alanine amidase and either a D-alanyl-glycyl endopeptidase or a glycyl-glycyl endopeptidase, to yield the fragment $A_2QKG_5$ (single letter amino acid code) (FIG. 6, Plate B).

Figure 6:
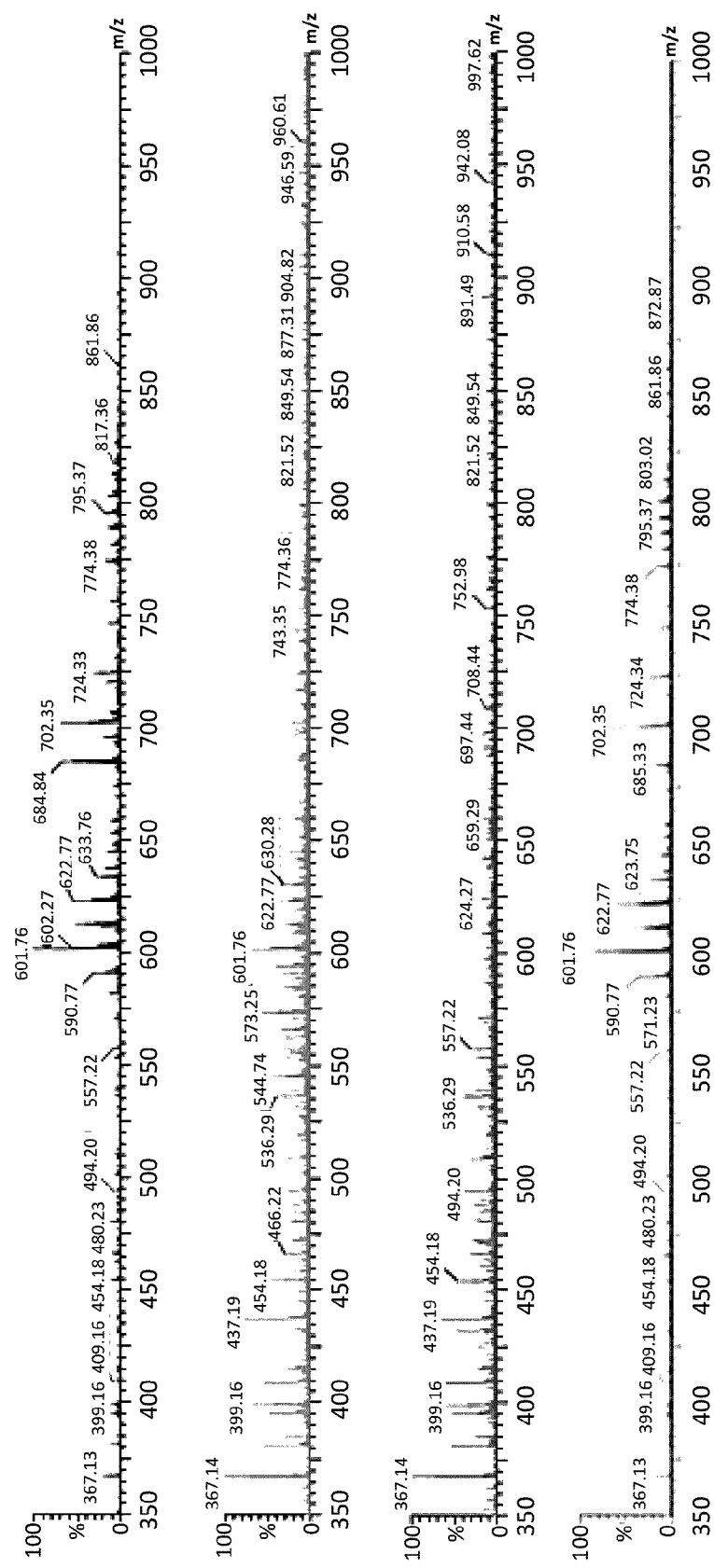
FIG. 6 illustrates the catalytic mechanism of PlyGRCS.
Figure 6:
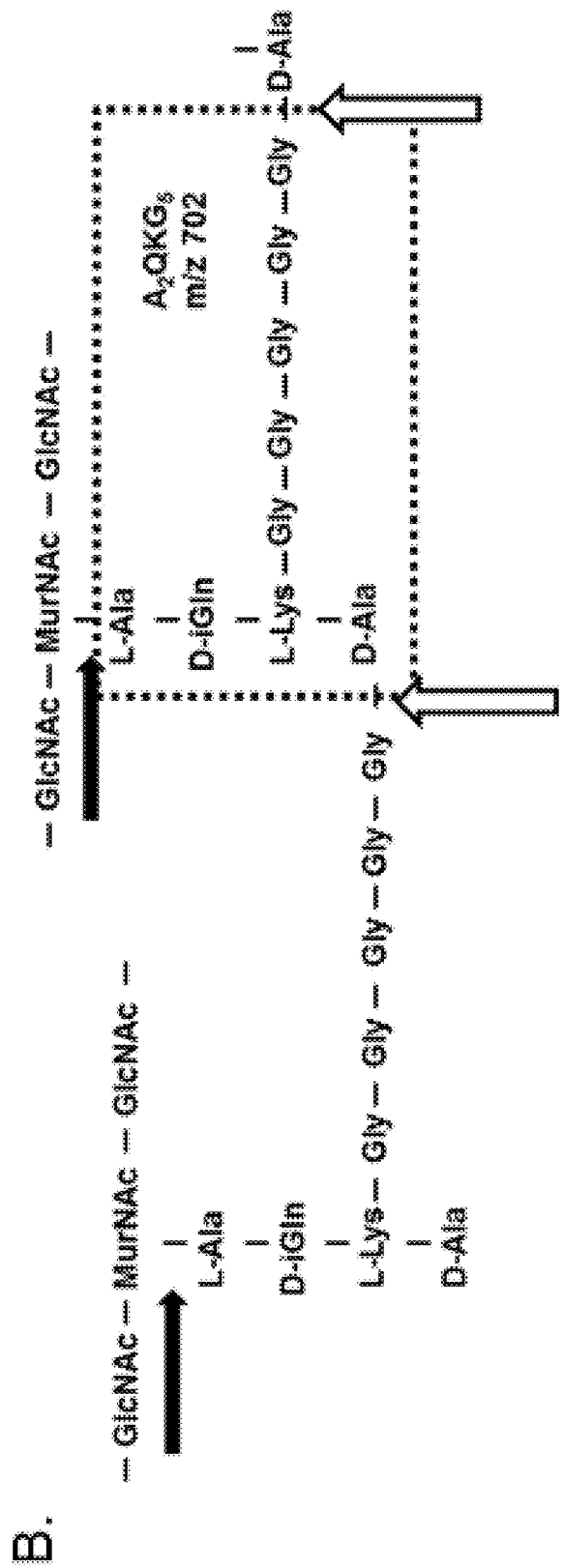
Figure 6:
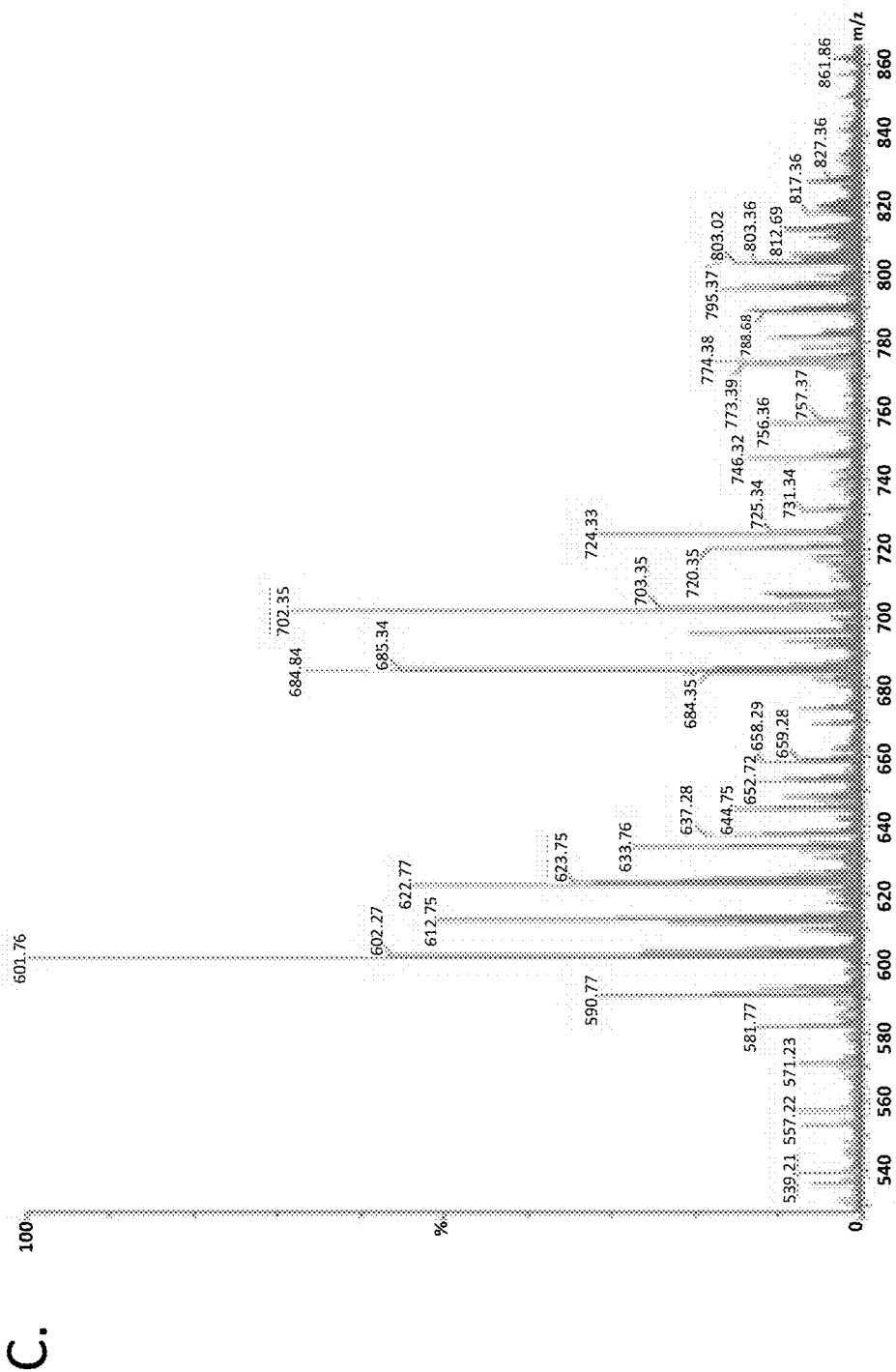

Moreover, a larger double-charged ion (m/z=684.84) was also observed that likely corresponds to the fragment $A_4Q_2K_2G_{10}$ (without a water molecule), resulting from incomplete peptidoglycan digest (FIG. 6, Plates A and C). Presence of the 702.35 and 684.84 peaks was reproducible on independent digests and ESI-MS experiments. Control experiments with peptidoglycan digested with the 2638A amidase domain, a known N-acetylmuramoyl-L-alanine amidase (FIG. 6, Plate A, second spectrum), or undigested peptidoglycan (FIG. 6, Plate A, third spectrum) did not contain the 702.35 or 684.84 peaks indicating that generation of the 702.35 and 684.84 fragments by PlyGRCS was not an artifact of a single enzymatic activity acting on uncrosslinked or partially cleaved peptidoglycan.

Furthermore, a double digest with PlyGRCS and CHAP-K, which has D-alanyl-glycyl endopeptidase activity (Becker S C et al. (2009) *LysK CHAP endopeptidase domain is required for lysis of live staphylococcal cells*. FEMS Microbiol Lett 294(1):52-60) was performed to elucidate the specific nature of the endopeptidase activity. Because this spectrum was identical to that of the PlyGRCS alone digested peptidoglycan, it was determined that PlyGRCS possesses a D-alanyl-glycyl endopeptidase activity, as a glycyl-glycyl endopeptidase activity would have yielded a different fragment pattern.

Thus, these data indicate that PlyGRCS, which has a single catalytic CHAP domain, can cleave two distinct bonds in the staphylococcal peptidoglycan.

Discussion

The use of endolysins provides a targeted treatment for bacterial infections that circumvents traditional antibiotic resistance mechanisms (Spratt B G (1994) *Resistance to antibiotics mediated by target alterations*. Science 264 (5157):388-93). In accordance with embodiments of the present invention, PlyGRCS endolysin was characterized and demonstrated bacteriolytic activity against MRSA successfully. The endolysin dosage used demonstrated that the efficacy of PlyGRCS is comparable to or better than other published staphylococcal endolysins (Gilmer D B et al. (2013) *Novel bacteriophage lysin with broad lytic activity protects against mixed infection by Streptococcus pyogenes and methicillin-resistant Staphylococcus aureus*. Antimicrobial agents and chemotherapy 57(6):2743-50; Jun S Y et al. (2011) *Comparison of the antibacterial properties of phage endolysins SAL*-1 *and LysK*. Antimicrobial agents and chemotherapy 55(4):1764-7; Sass P & Bierbaum G (2007) *Lytic activity of recombinant bacteriophage phi*11 *and phi*12 *endolysins on whole cells and biofilms of Staphylococcus aureus*. Appl Environ Microbiol 73(1):347-52). Moreover, because the optimal conditions for PlyGRCS activity were determined to be in the physiological range, this enzyme is suitable for use as an antimicrobial agent.

Even more impressive is the ability of PlyGRCS to act against stationary phase staphylococci as well as medically relevant biofilms, a further hindrance to traditional antibiotic therapy. Given the ability of endolysins like PlyGRCS to disrupt biofilms, they could be utilized in conjunction with classical antibiotics. In some embodiments, the endolysin provides the initial disturbance to the biofilm structure, thereby allowing the antibiotic to subsequently access the now susceptible target bacteria. Antibiotics applied in combination with endolysins bind more efficiently to their planktonic target bacterial cells, and thus this same phenomenon may be observed in biofilms as well (Schuch R et al. (2013) *Combination therapy with lysin CF*-301 *and antibiotic is superior to antibiotic alone for treating methicillin-resistant Staphylococcus aureus-induced murine bacteremia*. J Infect Dis 2014:209).

Identification of the PlyGRCS cleavage sites is also an important finding. This is believed to be the first demonstration of a single CHAP domain, or any individual endolysin catalytic domain, that possesses the ability to cleave two disparate bonds in the bacterial peptidoglycan. Initially, it was thought that the results were attributed to a single cleavage of uncrosslinked peptidoglycan, resulting in a fragment that appeared to be created by two cleavage events. However, spectra from repeated experiments on undigested control peptidoglycan and control digests with enzymes of known specificity collectively indicate that PlyGRCS is capable of liberating the fragment $A_2QKG_5$ from the staphylococcal peptidoglycan. This would necessitate cleavage of the amide bond formed between MurNAc and Ala residues as well as the hydrolysis of the amide bond formed between D-Ala and Gly residues or one of the Gly-Gly bonds. Further experiments with a double digest including PlyGRCS and CHAP-K, a D-alanyl-glycyl endopeptidase, showed an identical pattern to the PlyGRCS only spectrum, indicating that the endopeptidase activity of PlyGRCS is identical to CHAP-K.

While these findings indicating both amidase and endopeptidase activities associated with the single CHAP domain-containing PlyGRCS were surprising, other CHAP domains have been associated with an N-acetylmuramoyl-L-alanine amidase activity in the streptococcal PlyC endolysin (McGowan S et al. (2012) *X-ray crystal structure of the streptococcal specific phage lysin PlyC*. Proc Natl Acad Sci USA 109(31):12752-7) as well as D-alanyl-glycyl endopeptidase activity in multiple staphylococcal endolysins (Schmelcher M et al. (2012) *Bacteriophage endolysins as novel antimicrobials*. Future Microbiol 7(10):1147-71). Moreover, the recently crystallized CHAP domain from the staphylococcal endolysin LysGH15 shows highest structural homology to the aforementioned CHAP domain of PlyC, with a root-mean-square deviation (RMSD)=2.32 Å (Gu J et al. (2014) *Structural and biochemical characterization reveals LysGH*15 *as an unprecedented "EF-Hand-like" calcium-binding phage lysin*. PLoS pathogens 10(5): e1004109), further supporting the conclusion that these domains exhibit multiple activities. Finally, consistent with the findings of our biochemical assays, both amidase and endopeptidase activities would yield free amine groups via cleavage of peptide moieties and additionally would not liberate reducing sugars, which requires the cleavage of at least one of the two glycosidic bonds responsible for maintaining the glycan backbone of peptidoglycan.

The implications of a single catalytic domain with two cleavage specificities are numerous for bioengineering efforts. First, endolysins display synergy with other endolysins of different cleavage specificities. For example, killing of pneumococci is enhanced when the endolysins Cpl-1, an N-acetylmuramidase, and PAL, an N-acetylmuramoyl-L-alanine amidase, are used together compared to twice the concentration of either enzyme alone (Loeffler J M & Fischetti V A (2003) *Synergistic lethal effect of a combination of phage lytic enzymes with different activities on penicillin-sensitive and-resistant Streptococcus pneumoniae strains*. Antimicrobial agents and chemotherapy 47(1):375-7). Likewise, mutagenesis of active-site residues was used to show synergy between two catalytic domains, an N-acetylmuramoyl-L-alanine amidase and a glycosyl hydrolase, within the PlyC endolysin (McGowan S et al. (2012) *X-ray crystal structure of the streptococcal specific phage lysin PlyC*. Proc Natl Acad Sci USA 109(31):12752-7). It is believed that synergy arises from cleaving the peptidoglycan at two different locations, which is more destabilizing to the superstructure than repetitive cleavages at one location and would result in accelerated osmolysis of the bacterial cell. Additionally, cleavage of one bond may facilitate access to the second target, further contributing to this synergistic effect.

A second benefit of a catalytic domain with dual activities is that it is less susceptible to development of resistance. While there are currently no specific reports of bacterial strains developing resistance to phage-encoded endolysins, resistance to peptidoglycan hydrolases as a general class has been reported. Notably, modifications to the peptidoglycan backbone can render N-acetylmuramidases (i.e. lysozymes) ineffective (Davis K M & Weiser J N (2011) *Modifications to the peptidoglycan backbone help bacteria to establish infection*. Infect Immun 79(2):562-70; Vollmer W (2008) *Structural variation in the glycan strands of bacterial peptidoglycan*. FEMS Microbiol Rev 32(2):287-306). More specific to the staphylococcal peptidoglycan, resistance to lysostaphin, a bacterial derived glycyl-glycine endopeptidase, can be achieved by simple modification of the pentaglycine crossbridge in these species (Nelson D C et al. (2012) *Endolysins as antimicrobials*. Adv Virus Res 83:299-365). Thus, endolysins engineered to have more than one catalytic activity would circumvent resistance development targeting the specificity of one activity. As protein therapeutics, PlyGRCS is amenable to domain shuffling, directed evolution, and bioengineering approaches to further enhance efficacy and/or specificity. The unique dual substrate activity of the PlyGRCS catalytic domain thus offers an ideal model for identifying other domains from staphylococcal-specific endolysins.

All publications mentioned in this specification are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. A method of treating a Staphylococcal infection in a subject comprising administering to said subject a therapeutically effective amount of an isolated polypeptide comprising the amino acid sequence of SEQ ID NO: 6.

2. The method of claim 1, wherein said isolated polypeptide further comprises the amino acid sequence of SEQ ID NO: 7.

3. The method of claim 1, wherein said isolated polypeptide comprises the amino acid sequence of SEQ ID NO: 5.

4. The method of claim 1, comprising the further step of administering to said subject a secondary therapeutic agent after or concurrent with said administration of said isolated polypeptide.

5. The method of claim 4, wherein said secondary therapeutic agent is one or more antibiotic.

6. The method of claim 5, wherein said antibiotic is selected from the group consisting of a penicillin, a cephalosporin, a polymyxin, an ansamycin, a quinolone, a sulfonamide, a lipopeptide, a glycycline, and an oxazolidinone.

7. The method of claim 5, wherein said antibiotic is selected from the group consisting of linezolid, daptomycin, and tigecycline, vancomycin, fidaxomicin, and metronidazole.

8. The method of claim 1, wherein said Staphylococcal infection is caused by strain S. aureus.

* * * * *

SEQUENCE LISTING

```
<160> NUMBER OF SEQ ID NOS: 13

<210> SEQ ID NO 1
<211> LENGTH: 753
<212> TYPE: DNA
<213> ORGANISM: Staphylococcus aureus

<400> SEQUENCE: 1
atgaaatcac aacaacaagc aaaagaatgg atatataaac atgagggtac tggtgttgac      60
tttgatggtg catatggttt tcaatgtatg gacttagctg ttgcttatgt atattacatt     120
acagacggta aagttcgtat gtggggtaac gccaaagacg ctattaataa tgactttaaa     180
ggtttagcaa cggtgtatga aaatacaccg agctttaaac ctcaattagg tgacgttgct     240
gtttatacta attctcaata tggtcacatt caatgtgtaa taagtggtaa tttagattat     300
tatacatgtt tagagcaaaa ctggttaggt ggtgggtttg acggttggga aaaagcaaca     360
ataagaacac attattatga cggtgtaaca cactttatta gacctaaatt ttctgctagt     420
aatagtaatg tattagaaac atcaaaagta aatacatttg gaaattggaa acaaaaccaa     480
tacggaacat attacagaaa tgaaaatgca acatttacat gtggattttt accaatattt     540
gcacgtgtag gtagtcctaa attaagtgaa cctaatggat attggttcca accaaatggt     600
tatacaccat atgacgaagt ttgtttatca gatggactag tgtggattgg ttataattgg     660
caaggaacac gttattattt accagtgaga caatggaacg gtaaaacggg taatagttat     720
agcattggtt taccctgggg ggtgttctca taa                                  753

<210> SEQ ID NO 2
<211> LENGTH: 771
<212> TYPE: DNA
<213> ORGANISM: Staphylococcus aureus

<400> SEQUENCE: 2
atgaaatcac aacaacaagc aaaagaatgg atatataaac atgagggtac tggtgttgac      60
tttgatggtg catatggttt tcaatgtatg gacttagctg ttgcttatgt atattacatt     120
acagacggta aagttcgtat gtggggtaac gccaaagacg ctattaataa tgactttaaa     180
ggtttagcaa cggtgtatga aaatacaccg agctttaaac ctcaattagg tgacgttgct     240
gtttatacta attctcaata tggtcacatt caatgtgtaa taagtggtaa tttagattat     300
tatacatgtt tagagcaaaa ctggttaggt ggtgggtttg acggttggga aaaagcaaca     360
```

```
ataagaacac attattatga cggtgtaaca cactttatta gacctaaatt ttctgctagt      420
aatagtaatg tattagaaac atcaaaagta aatacatttg gaaattggaa acaaaaccaa      480
tacggaacat attacagaaa tgaaaatgca acatttacat gtggatttt accaatattt       540 gcacgtgtag gtagtcctaa attaagtgaa cctaatggat attggttcca accaaatggt      600
tatacaccat atgacgaagt tgtttatca gatggactag tgtggattgg ttataattgg       660
caaggaacac gttattattt accagtgaga caatggaacg gtaaaacggg taatagttat      720
agcattggtt taccctgggg ggtgttctca catcatcatc atcatcatta a               771
```

<210> SEQ ID NO 3
<211> LENGTH: 753
<212> TYPE: DNA
<213> ORGANISM: Artificial Sequence
<220> FEATURE:
<223> OTHER INFORMATION: Synthetically generated polypeptide (PlyGRCS
      Codon Optimized (75% similarity to native))

<400> SEQUENCE: 3

```
atgaaatcac agcagcaggc taaagaatgg atttataaac atgaaggaac tggtgttgat      60
ttcgacggcg cttacgggtt tcagtgtatg gacctggccg tggcgtatgt gtactatatt      120
accgacggga agtccgtat gtggggtaat gcgaaggatg cgattaataa cgattttaaa       180
ggcttagcca cggtctatga aaatactccg tcatttaagc cgcagctggg ggacgtggcc      240
gtatatacga acagccagta tgggcatatc cagtgcgtga ttagcggaaa tctggactac      300
tacacgtgcc ttgaacagaa ctggctcggg ggagggttcg acggttggga aaaagcgact      360
atccgtaccc attattacga tggagtgacc cattttattc gtccgaagtt tagtgcttct      420
aacagcaatg ttctggaaac tagcaaggtg aatactttg gaaactggaa acagaatcag      480
tacggcacgt attatcggaa tgagaacgcc actttcacgt gtggtttcct gccgattttc      540
gctcgtgtcg gctcgcctaa attgtccgaa ccgaacggct attggttcca gccgaatggt      600 tatacccgt atgatgaggt gtgcttgtcc gacggtctgg tgtggatcgg ttacaactgg       660
cagggaaccc gttactacct tccggtgcgt cagtggaatg gcaaaacggg gaattcttac      720
tctattggac ttccatgggg cgttttttca taa                                   753
```

<210> SEQ ID NO 4
<211> LENGTH: 771
<212> TYPE: DNA
<213> ORGANISM: Artificial Sequence
<220> FEATURE:
<223> OTHER INFORMATION: Synthetically generated polypeptide (PlyGRCS
      Codon (optimized; 75% similarity to native; 6XHis tag))

<400> SEQUENCE: 4

```
atgaaatcac agcagcaggc taaagaatgg atttataaac atgaaggaac tggtgttgat      60
ttcgacggcg cttacgggtt tcagtgtatg gacctggccg tggcgtatgt gtactatatt      120
accgacggga agtccgtat gtggggtaat gcgaaggatg cgattaataa cgattttaaa       180
ggcttagcca cggtctatga aaatactccg tcatttaagc cgcagctggg ggacgtggcc      240
gtatatacga acagccagta tgggcatatc cagtgcgtga ttagcggaaa tctggactac      300
tacacgtgcc ttgaacagaa ctggctcggg ggagggttcg acggttggga aaaagcgact      360
atccgtaccc attattacga tggagtgacc cattttattc gtccgaagtt tagtgcttct      420
aacagcaatg ttctggaaac tagcaaggtg aatactttg gaaactggaa acagaatcag      480
tacggcacgt attatcggaa tgagaacgcc actttcacgt gtggtttcct gccgattttc      540
```

```
gctcgtgtcg gctcgcctaa attgtccgaa ccgaacggct attggttcca gccgaatggt    600 tatacccgt atgatgaggt gtgcttgtcc gacggtctgg tgtggatcgg ttacaactgg    660
cagggaaccc gttactacct tccggtgcgt cagtggaatg gcaaaacggg gaattcttac    720
tctattggac ttccatgggg cgttttttca caccaccacc accatcatta a           771
```

<210> SEQ ID NO 5
<211> LENGTH: 250
<212> TYPE: PRT
<213> ORGANISM: Artificial Sequence
<220> FEATURE:
<223> OTHER INFORMATION: Synthetically generated polypeptide (PlyGRCS
      phage (S. aureus))

<400> SEQUENCE: 5

```
Met Lys Ser Gln Gln Gln Ala Lys Glu Trp Ile Tyr Lys His Glu Gly
1               5                   10                  15

Thr Gly Val Asp Phe Asp Gly Ala Tyr Gly Phe Gln Cys Met Asp Leu
            20                  25                  30

Ala Val Ala Tyr Val Tyr Tyr Ile Thr Asp Gly Lys Val Arg Met Trp
        35                  40                  45

Gly Asn Ala Lys Asp Ala Ile Asn Asn Asp Phe Lys Gly Leu Ala Thr
    50                  55                  60

Val Tyr Glu Asn Thr Pro Ser Phe Lys Pro Gln Leu Gly Asp Val Ala
65                  70                  75                  80

Val Tyr Thr Asn Ser Gln Tyr Gly His Ile Gln Cys Val Ile Ser Gly
                85                  90                  95

Asn Leu Asp Tyr Tyr Thr Cys Leu Glu Gln Asn Trp Leu Gly Gly Gly
            100                 105                 110

Phe Asp Gly Trp Glu Lys Ala Thr Ile Arg Thr His Tyr Tyr Asp Gly
        115                 120                 125

Val Thr His Phe Ile Arg Pro Lys Phe Ser Ala Ser Asn Ser Asn Val
    130                 135                 140

Leu Glu Thr Ser Lys Val Asn Thr Phe Gly Asn Trp Lys Gln Asn Gln
145                 150                 155                 160

Tyr Gly Thr Tyr Tyr Arg Asn Glu Asn Ala Thr Phe Thr Cys Gly Phe
                165                 170                 175

Leu Pro Ile Phe Ala Arg Val Gly Ser Pro Lys Leu Ser Glu Pro Asn
            180                 185                 190

Gly Tyr Trp Phe Gln Pro Asn Gly Tyr Thr Pro Tyr Asp Glu Val Cys
        195                 200                 205

Leu Ser Asp Gly Leu Val Trp Ile Gly Tyr Asn Trp Gln Gly Thr Arg
    210                 215                 220

Tyr Tyr Leu Pro Val Arg Gln Trp Asn Gly Lys Thr Gly Asn Ser Tyr
225                 230                 235                 240

Ser Ile Gly Leu Pro Trp Gly Val Phe Ser
                245                 250
```

<210> SEQ ID NO 6
<211> LENGTH: 140
<212> TYPE: PRT
<213> ORGANISM: Artificial Sequence
<220> FEATURE:
<223> OTHER INFORMATION: Synthetically generated polypeptide (CHAPGRCS
      (amino acids 1-140))

<400> SEQUENCE: 6

```
Met Lys Ser Gln Gln Ala Lys Glu Trp Ile Tyr Lys His Glu Gly
1               5                   10                  15

Thr Gly Val Asp Phe Asp Gly Ala Tyr Gly Phe Gln Cys Met Asp Leu
            20                  25                  30

Ala Val Ala Tyr Val Tyr Tyr Ile Thr Asp Gly Lys Val Arg Met Trp
            35                  40                  45

Gly Asn Ala Lys Asp Ala Ile Asn Asn Asp Phe Lys Gly Leu Ala Thr
            50                  55                  60

Val Tyr Glu Asn Thr Pro Ser Phe Lys Pro Gln Leu Gly Asp Val Ala
65                  70                  75                  80

Val Tyr Thr Asn Ser Gln Tyr Gly His Ile Gln Cys Val Ile Ser Gly
                85                  90                  95

Asn Leu Asp Tyr Tyr Thr Cys Leu Glu Gln Asn Trp Leu Gly Gly Gly
                100                 105                 110

Phe Asp Gly Trp Glu Lys Ala Thr Ile Arg Thr His Tyr Tyr Asp Gly
            115                 120                 125

Val Thr His Phe Ile Arg Pro Lys Phe Ser Ala Ser
            130                 135                 140
```

```
<210> SEQ ID NO 7
<211> LENGTH: 100
<212> TYPE: PRT
<213> ORGANISM: Artificial Sequence
<220> FEATURE:
<223> OTHER INFORMATION: Synthetically generated polypeptide (SH3_5GRCS
      (amino acids 150-250))

<400> SEQUENCE: 7
```

```
Asn Thr Phe Gly Asn Trp Lys Gln Asn Gln Tyr Gly Thr Tyr Tyr Arg
1               5                   10                  15

Asn Glu Asn Ala Thr Phe Thr Cys Gly Phe Leu Pro Ile Phe Ala Arg
            20                  25                  30

Val Gly Ser Pro Lys Leu Ser Glu Pro Asn Gly Tyr Trp Phe Gln Pro
            35                  40                  45

Asn Gly Tyr Thr Pro Tyr Asp Glu Val Cys Leu Ser Asp Gly Leu Val
            50                  55                  60

Trp Ile Gly Tyr Asn Trp Gln Gly Thr Arg Tyr Tyr Leu Pro Val Arg
65                  70                  75                  80

Gln Trp Asn Gly Lys Thr Gly Asn Ser Tyr Ser Ile Gly Leu Pro Trp
                85                  90                  95

Gly Val Phe Ser
            100
```

```
<210> SEQ ID NO 8
<211> LENGTH: 47
<212> TYPE: DNA
<213> ORGANISM: Artificial Sequence
<220> FEATURE:
<223> OTHER INFORMATION: Primer (CHAP-F)

<400> SEQUENCE: 8
ggggaattca ttatgaaatc acaacaacaa gcaaaagaat ggatata          47

<210> SEQ ID NO 9
<211> LENGTH: 47
<212> TYPE: DNA
<213> ORGANISM: Artificial Sequence
<220> FEATURE:
<223> OTHER INFORMATION: Primer (CHAP-R)
```

```
<400> SEQUENCE: 9
aaatctagat taatgatgat gatgatgatg actagcagaa aatttag                47

<210> SEQ ID NO 10
<211> LENGTH: 48
<212> TYPE: DNA
<213> ORGANISM: Artificial Sequence
<220> FEATURE:
<223> OTHER INFORMATION: Primer (SH3_5F)

<400> SEQUENCE: 10
ggggaattca ttatgaatac atttggaaat tggaaacaaa accaatac               48

<210> SEQ ID NO 11
<211> LENGTH: 47
<212> TYPE: DNA
<213> ORGANISM: Artificial Sequence
<220> FEATURE:
<223> OTHER INFORMATION: Primer (SH3_5R)

<400> SEQUENCE: 11
aaatctagat taatgatgat gatgatgatg tgagaacacc ccccaag                47

<210> SEQ ID NO 12
<211> LENGTH: 33
<212> TYPE: DNA
<213> ORGANISM: Artificial Sequence
<220> FEATURE:
<223> OTHER INFORMATION: Primer (C29S)

<400> SEQUENCE: 12
gcatatggtt ttcaaagcat ggacttagct gtt                               33

<210> SEQ ID NO 13
<211> LENGTH: 33
<212> TYPE: DNA
<213> ORGANISM: Artificial Sequence
<220> FEATURE:
<223> OTHER INFORMATION: Primer (H92A)

<400> SEQUENCE: 13
aattctcaat atggtgcgat tcaatgtgta ata                               33
```